US011668722B2

(12) United States Patent
Kettenberger et al.

(10) Patent No.: US 11,668,722 B2
(45) Date of Patent: Jun. 6, 2023

(54) ANTIBODY SELECTION METHOD

(71) Applicant: Hoffmann-La Roche Inc., Little Falls, NJ (US)

(72) Inventors: Hubert Kettenberger, Penzberg (DE); Wolfgang Richter, Basel (CH); Laurent Lariviere, Penzberg (DE); Thomas Kraft, Penzberg (DE); Thomas Emrich, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 246 days.

(21) Appl. No.: 16/657,753

(22) Filed: Oct. 18, 2019

(65) Prior Publication Data

US 2020/0217851 A1 Jul. 9, 2020

Related U.S. Application Data

(63) Continuation of application No. PCT/EP2018/060536, filed on Apr. 25, 2018.

(30) Foreign Application Priority Data

Apr. 28, 2017 (EP) .................................... 17168633
Dec. 21, 2017 (EP) .................................... 17209268

(51) Int. Cl.
*G01N 33/68* (2006.01)
*C07K 16/18* (2006.01)
*C07K 16/28* (2006.01)

(52) U.S. Cl.
CPC .......... *G01N 33/686* (2013.01); *C07K 16/18* (2013.01); *C07K 16/2863* (2013.01)

(58) Field of Classification Search
CPC ... C07K 16/18; C07K 16/2863; G01N 33/686
See application file for complete search history.

(56) References Cited

U.S. PATENT DOCUMENTS

2002/0004587 A1 1/2002 Miller et al.
2017/0227547 A1* 8/2017 Emrich .............. G01N 33/6854

FOREIGN PATENT DOCUMENTS

JP 2015-512034 A 4/2015
OA 96/027011 A1 9/1996
WO 2013/120929 A1 5/2013
WO 2014/177460 A1 11/2014
WO 2015/140126 A1 9/2015
WO 2015/175874 A2 11/2015
WO 2016/071376 A2 5/2016

OTHER PUBLICATIONS

Kraft., Heparin chromatography as an in vitro predictor for antibody clearance rate through pinocytosis. MABS 12 (i): e1683432, 9 pages, 2020.*

Schlothauer et al., Analytical FcRn affinity chromatography for functional characterization of monoclonal antibodies. MABS 5 (4): 576-586, 2013.*

Datta-Mannan et al., Monoclonal antibody clearance: impact of modulating the interaction of IgG with the neonatal Fc receptor. J. Biol. Chem. 282 (3): 1709-1717, 2007.*

Datta-Mannan, Amita et al., "Aberrant bispecific antibody pharmacokinetics linked to liver sinusoidal endothelium clearance mechanism in cynomolgus monkeys" MAbs 8(5):696-982 ( 2016).

Datta-Mannan, Amita et al., "Balancing charge in the complementarity-determining regions of humanized mAbs without affecting pI reduces non-specific binding and improves the pharmacokinetics" MAbs 7(3):483-493 ( 2015).

Akilesh et al., "Neonatal FcR Expression in Bone Marrow-Derived Cells Functions to Protect Serum IgG from Catabolism1" J. Immunol. 179:4580-4588 ( 2007).

Atwell et al., "Stable Heterodimers from Remodeling the Domain Interface of a Homodimer using a Phage Dispaly Library" J. Mol. Biol. 270:26-35 ( 1997).

Brambell et al. et al., "A Theoretical Model of γ-Globulin Catabolism" Nature 203:1352-1354 ( 1964).

Carter, P., et al., antibody "'Knobs-into-holes' provides a rational design strategy for engineering antibody CH3 domains for heavy chain heterodimerization" Immunotechnology 2(1):73 (Jan. 1996).

Chaudhury et al., "The Major Histocompatibility Complex—related Fc Receptor for IgG (FcRn) Binds Albumin and Prolongs Its Lifespan" J. Exp. Med. 197:315-322 ( 2003).

Clackson et al., "Making antibody fragments using phage display libraries" Nature 352:624-628 (Aug. 15, 1991).

Datta-Mannan et al., "The interplay of non-specific binding, target-mediated clearance and FcRn interactions on the pharmacokinetics of humanized antibodies" MABS 7(6):1084-1093 ( 2015).

Edelman et al., "Antibody structure and molecular immunology" J. Immunol 34:1-22 ( 1991).

Ghetie and Ward, "Multiple Roles for the Major Histocompatibility Complex Class I-Related Receptor FcRn" Annu. Rev. Immunol. 18:739-766 ( 2000).

Goebl et al., "Neonatal Fc Receptor Mediates Internalization of Fc in Transfected Human Endothelial Cells" Mol. Biol Cell 19:5490-5505 ( 2008).

Hotzel et al., "A strategy for risk mitigation of antibodies with fast clearance" MABS 4(6):753-760 ( 2012).

Huber et al., "Crystallization and stoichiometry of binding of a complex between a rat intestinal Fc receptor and Fc" J. Mol. Biol. 230:1077-1083 ( 1993).

(Continued)

*Primary Examiner* — Ruixiang Li

(57) ABSTRACT

Herein is reported a method for selecting an antibody with a systematic clearance in cynomolgus monkeys of less than 8 mL/kg/day comprising the steps of measuring the retention time of the antibody on performing an FcRn affinity chromatography with a positive linear pH gradient and on a heparin affinity chromatography with a positive linear conductivity/salt gradient, and selecting an antibody that has a relative retention time on the FcRn affinity chromatography column is less than 1.78 times the retention time difference between peaks 2 and 3 the retention time of preparation of an oxidized anti-Her3 antibody of SEQ ID NO: 03 and 04, and a relative retention time on the heparin affinity chromatography column is less than 0.87 times the retention time of an anti-pTau antibody of SEQ ID NO: 01 and 02.

7 Claims, 10 Drawing Sheets

Specification includes a Sequence Listing.

(56) References Cited

OTHER PUBLICATIONS

International Preliminary Report on Patentability for PCT/EP2018/060536 dated Oct. 29, 2019.
International Search Report for PCT/EP2018/060536 dated Jul. 12, 2018.
Kim et al., "Identifying Amino Acid Residues that Influence Plasma Clearance of Murine IgG1 Fragments by Site-Directed Mutagenesis." Eur. J. Immunol. 24:542-548 ( 1994).
Kuo et al., "Neonatal Fc receptor: from immunity to therapeutics" J. Clin. Immunol. 30:777-789 ( 2010).
Martin et al., "Crystal structure at 2.8 A of an FcRn/heterodimeric Fc complex: mechanism of pH-dependent binding" Mol. Cell 7(4):867-877 (Apr. 2001) .
Martin et al., "Peer Reviewed: Nanomaterials in Analytical Chemistry" Analytical Chemistry News & Features 70:322A-327A (May 1, 1998).
Merchant et al., "An efficient route to human bispecific IgG" Nat. Biotechnol. 16(7):677-681 ( 1998).
Montoyo et al., "Conditional deletion of the MHC class I-related receptor FcRn reveals the sites of IgG homeostasis in mice" PNAS 106:2788-2793 ( 2009).
Neuber et al., "Characterization and screening of IgG binding to the neonatal Fc receptor" MABS 6(4):928-942 ( 2014)
Ober et al., "Exocytosis of IgG as mediated by the receptor, FcRn: an Analysis at the Single-Molecule Level" Proc Natl. Acad. Sci. U.S.A. 101(30):11076-11081. (Jul. 2004).
Ober et al., "Visualizing the Site and Dynamics of IgG Salvage by the MHC Class I-Related Receptor, FcRn1" J. Immunol. 172:2021-2029 ( 2004).
Portolano, S., et al., "Lack of promiscuity in autoantigen-specific H and L chain combinations as revealed by human H and L chain 'roulette'" J. Immunol. 150(3):880-887 (Feb. 1, 1993).
Putnam et al., "Pharmacokinetic, pharmacodynamic and immunogenicity comparability assessment strategies for monoclonal antibodies" Trends Biotechnol 28:509-516 ( 2010).
Reff et al., "A review of modifications to recombinant antibodies: attempt to increase efficacy in oncology applications" Crit. Rev. Oncol. Hematol. 40:25-35 ( 2001).
Ridgway et al., "'Knobs-into-holes' Engineering of Antibody CH3 Domains for Heavy Chain Heterodimerization" Protein Eng. 9(7):617-621 ( 1996).
Rodewald et al., "ph-dependent binding of immunoglobulins to intestinal cells of the neonatal rat" J. Cell Biol. 71:666-669 (Nov. 1976).
Roopenian and Akilesh, "FcRn: the neonatal Fc receptor comes of age" Nat. Rev. Immunol. 7:715-725 ( 2007).
Roopenian et al., "The MHC Class I-like IgG receptor controls perinatal IgG transport, IgG homestasis, and fate of IgG fc-copled drugs" J. Immunol. 170(7):3528-3533 (Apr. 2003).
Sampei et al., "Identification and multidimensional optimization of an asymmetric bispecific IgG antibody mimicking the function of factor VIII cofactor activity" PLOS ONE 8(2):e57479 ( 2013).
Sanchez et al., "Stoichiometry of the Interaction between the Major Histocompatibility Complex-Related Fc Receptor and Its Fc Ligand" Biochemistry 38:9471-9476 ( 1999).
Schlothauer, T., et al., "Analytical FcRn affinity chromatography for functional characterization of monoclonal antibodies" MABS5(4):576-586 ( 2013).
Schoch et al., "Charge-mediated influence of the antibody variable domain on FcRn-dependent pharmacokinetics" PNAS 112(19):5997-6002 ( 2015) .
Stracke et al., "A novel approach to investigate the effect of methionine oxidation on pharmacokinetic properties of therapeutic antibodies" MABS 6:1229-1242 ( 2014).
Vaccaro et al., "Engineering the Fc region of immunoglobulin G to modulate in vivo antibody levels" Nat. Biotechnol. 23:1283-1288 ( 2005).
Waldmann and Strober, "Metabolism of Immunoglobulins" Prog. Allergy13:1-110 ( 1969).

* cited by examiner

ANTIBODY SELECTION METHOD

CROSS-REFERENCE TO RELATED APPLICATIONS

This application is a continuation of International Application No. PCT/EP2018/060536, filed Apr. 25, 2018, which claims benefit of priority to EP Application No. 17168633.0 filed Apr. 28, 2017 and EP Application No. 17209268.6, filed Dec. 21, 2017, each of which are incorporated herein by reference in its entirety.

SEQUENCE LISTING

The instant application contains a Sequence Listing submitted electronically in ASCII format and is hereby incorporated herein by reference in its entirety. Said ASCII copy, created Oct. 16, 2019, is named P34254-US_Sequence_Listing.txt and is 73,038 bytes in size.

The current invention is in the field of recombinant antibody technology. Herein is reported a method for the selection of an antibody based on the retention times on two orthogonal affinity columns, namely on an FcRn affinity chromatography column and a heparin affinity chromatography column.

BACKGROUND OF THE INVENTION

Human immunoglobulins of the class G (IgGs) contain two antigen binding (Fab) regions that convey specificity for the target antigen and a constant region (Fc-region) that is responsible for interactions with Fc receptors (see e.g. Edelman, G. M., Scand. J. Immunol. 34 (1991) 1-22; Reff, M. E. and Heard, C., Crit. Rev. Oncol. Hematol. 40 (2001) 25-35). Human IgGs of subclasses IgG1, IgG2 and IgG4 have an average serum half-life of 21 days, which is longer than that of any other known serum protein (see, e.g., Waldmann, T. A. and Strober, W., Prog. Allergy 13 (1969) 1-110). This long half-life is predominantly mediated by the interaction between the Fc-region and the neonatal Fc receptor (FcRn) (see, e.g. Ghetie, V. and Ward, E. S., Annu. Rev. Immunol. 18 (2000) 739-766; Chaudhury, C., et al., J. Exp. Med. 197 (2003) 315-322.). This is one of the reasons, why IgGs or Fc-containing fusion proteins are used as a widespread class of therapeutics.

The neonatal Fc receptor FcRn is a membrane-associated receptor involved in both IgG and albumin homeostasis, in maternal IgG transport across the placenta and in antigen-IgG immune complex phagocytosis (see, e.g., Brambell, F. W., et al., Nature 203 (1964) 1352-1354; Ropeenian, D. C., et al., J. Immunol. 170 (2003) 3528-3533). Human FcRn is a heterodimer consisting of the glycosylated class I major histocompatibility complex-like protein ($\alpha$-FcRn) and a $\beta_2$ microglobulin ($\beta_2$m) subunit (see, e.g., Kuo, T. T., et al., J. Clin. Immunol. 30 (2010) 777-789). FcRn binds to a site in the $C_H2$-$C_H3$ region of the Fc-region (see, e.g., Ropeenian, D. C. and Akilesh, S., Nat. Rev. Immunol. 7 (2007) 715-725; Martin, W. L., et al., Mol. Cell 7 (2001) 867-877; Goebl, N. A., et al., Mol. Biol. Cell 19 (2008) 5490-5505; Kim, J. K., et al., Eur. J. Immunol. 24 (1994) 542-548.) and two FcRn molecules can bind to the Fc-region simultaneously (see, e.g., Sanchez, L. M., et al., Biochemistry 38 (1999) 9471-9476; Huber, A. H., et al., J. Mol. Biol. 230 (1993) 1077-1083.). The affinity between the FcRn and the Fc-region is pH dependent, showing nanomolar affinity at endosomal pH of 5-6 and rather weak binding at a physiological pH of 7.4 (see, e.g., Goebl, N. A., et al., Mol. Biol. Cell 19 (2008) 5490-5505; Ober, R. J., et al., Proc. Natl. Acad. Sci. USA 101 (2004) 11076-11081; Ober, R. J., et al., J. Immunol. 172 (2004) 2021-2029). The underlying mechanism conveying long half-life to IgGs can be explained by three fundamental steps. First, IgGs are subject to unspecific pinocytosis by various cell types (see, e.g., Akilesh, S., et al., J. Immunol. 179 (2007) 4580-4588; Montoyo, H. P., et al., Proc. Natl. Acad. Sci. USA 106 (2009) 2788-2793.). Second, IgGs encounter and bind FcRn in the acidic endosome at a pH of 5-6, thereby protecting IgGs from lysosomal degradation (see, e.g., Ropeenian, D. C. and Akilesh, S., Nat. Rev. Immunol. 7 (2007) 715-725; Rodewald, R., J. Cell Biol. 71 (1976) 666-669). Finally, IgGs are released in the extracellular space at physiological pH of 7.4 (see, e.g., Ghetie, V. and Ward, E. S., Annu. Rev. Immunol. 18 (2000) 739-766). This strict pH-dependent bind-and-release mechanism is critical for IgG recycling and any deviation of the binding characteristics at different pH values may strongly influence circulation half-life of IgGs (see, e.g., Vaccaro, C., et al., Nat. Biotechnol. 23 (2005) 1283-1288).

Hoetzel, I., et al. (mAbs 4 (2012) 753-760) disclosed a strategy for risk mitigation of antibodies with fast clearance as a majority of human therapeutic antibody candidates show pharmacokinetic properties suitable for clinical use, but an unexpectedly fast antibody clearance is sometimes observed that may limit the clinical utility. It is described an assay based on ELISA detection of binding to baculovirus (BV) particles to evaluate the non-specific binding of therapeutic proteins.

Analytical FcRn affinity chromatography for functional characterization of monoclonal antibodies is disclosed in WO 2013/120929. Pharmacokinetic, pharmacodynamic and immunogenicity comparability assessment strategies for monoclonal antibodies are disclosed by Putnam, W. S., et al. (Trends Biotechnol. 28 (2010) 509-516).

Sampei, Z., et al. (PLoS One 8 (2013) e57479) disclose the identification and multidimensional optimization of an asymmetric bispecific IgG antibody mimicking the function of factor VIII cofactor activity.

WO 2015/140126 discloses a method for the prediction of the in vivo half-life of an antibody based on the retention time determined on an FcRn affinity chromatography column.

Current literature discloses the use of FcRn chromatography (see, e.g., Schoch, A., et al., Proc. Natl. Acad. Sci. USA 112 (2015) 5997-6002) or FcRn affinity (see, e.g., Neuber, T., et al., MAbs 6 (2014) 928-942) as predictive for pharmacokinetics. Alternatively, heparin binding, e.g. in ELISA format (see, e.g., Datta-Mannan, A., et al., MAbs 7 (2015) 1084-1093) is disclosed as a surrogate parameter to quantify non-specific interactions with cell surface structures.

SUMMARY OF THE INVENTION

With the method according to the current invention it is possible to identify an increased number of, i.e. more, antibodies with suitable pharmacokinetic properties for a therapeutic application; especially it is possible to more correctly select antibodies with pharmacokinetic properties suitable for a therapeutic application. This is done by evaluating antibodies from a provided multitude of antibodies based on the results obtained with a method as reported herein.

It has been found that the selection of antibodies with respect to/based on their clearance in cynomolgus single-dose pharmacokinetic (SDPK) studies can be improved by using a combination of FcRn and heparin affinity chromatography, compared to isolated (1-dimensional) FcRn or isolated heparin chromatography, respectively. The improvement amongst other things lies in the reduction of the number of deselected antibodies with acceptable PK properties.

It has been found that the combination of FcRn affinity chromatography and heparin affinity chromatography allows defining FcRn and heparin affinity chromatography column retention time thresholds and thereby a two-dimensional retention time region, wherein antibodies with slow clearance, i.e. long systemic circulation half-live, can be found. Thus, this combination allows amongst other things for an improved selection of antibodies with long systemic circulation half-live, for an improvement in the accuracy of pharmacokinetic prediction, and for a reduction of the number of antibodies deselected despite having a long systemic circulation half-live.

It has been found that when the retention times on an FcRn affinity chromatography column and on a heparin affinity chromatography column are normalized based on the retention times of reference antibodies on the respective columns, a relative retention time region comprising predominantly antibodies with slow clearance is defined. This region is defined by a relative retention time on the FcRn affinity chromatography column of less than 1.78 (with an oxidized ($H_2O_2$-treated) anti-Her3 antibody preparation as reference antibody) and by a relative retention time on the heparin affinity chromatography column of less than 0.87 (with an anti-pTau antibody as reference antibody).

Thus, the current invention comprises a method for selecting an antibody with a systemic clearance in cynomolgus monkeys suitable to be used as therapeutic agent (in humans) comprising the following steps:

a) optionally providing a (ex-vivo; artificial) sample comprising the antibody,
b) performing an FcRn affinity chromatography with a positive linear pH gradient and a heparin affinity chromatography with a positive linear conductivity/salt gradient, and
c) selecting the antibody
   i) if/when the relative retention time of the antibody on the FcRn affinity chromatography column with respect to the retention time of a first reference antibody on the FcRn affinity chromatography column is less than a first threshold value, and
   ii) if/when the ratio of the retention time of the antibody on the heparin affinity chromatography column to the retention time of a second reference antibody on the heparin affinity chromatography column is less than a second threshold value.

In one embodiment the first reference antibody is an oxidized antibody preparation. In one embodiment the oxidized antibody preparation is a preparation comprising the reference antibody with respect to the methionine residues at position 252 in the heavy chain CH2 domains in non-oxidized form, in mono-oxidized form (only one of the two methionins at position 252 is oxidized) and in bi-oxidized form (both methionine residues at position 252 are oxidized) (numbering according to Kabat). In one embodiment the relative retention time is calculated based on the following formula $$t_{rel,i} = \frac{t_i - t_{reference\ antibody\ mono\text{-}oxidized\ peak}}{t_{reference\ antibody\ non\text{-}oxidized\ peak} - t_{reference\ antibody\ mono\text{-}oxidized\ peak}}$$

with $t_{rel,i}$=relative retention time of the antibody; $t_i$=retention time of the antibody. In one embodiment the first reference antibody is an anti-Her3 antibody that has a heavy chain with the amino acid sequence of SEQ ID NO: 03 and a light chain with the amino acid sequence of SEQ ID NO: 04. In one embodiment the first threshold value is 2. In one embodiment the first threshold value is 1.8. In one embodiment the first threshold value is 1.78.

In one embodiment the second reference antibody is an anti-pTau antibody that has a heavy chain with the amino acid sequence of SEQ ID NO: 01 and a light chain with the amino acid sequence of SEQ ID NO: 02. In one embodiment the second threshold value is 1. In one embodiment the second threshold value is 0.8. In one embodiment the second threshold value is 0.78.

In one embodiment step c) is selecting the antibody
   i) when/if the relative retention time on the FcRn affinity chromatography column is less than 1.78 times the retention time difference between peaks 2 and 3 of a preparation of an oxidized anti-Her3 antibody of SEQ ID NO: 03 and 04, and
   ii) when/if the relative retention time on the heparin affinity chromatography column is less than 0.87 times the retention time of an anti-pTau antibody of SEQ ID NO: 01 and 02.

In one embodiment a systematic clearance in cynomolgus monkey suitable for therapeutic application, i.e. the antibodies can be used as therapeutic agent, is 8 mL/kg/day or less. In one embodiment the systematic clearance is less than 8 mL/kg/day. In one embodiment the systematic clearance is less than 6 mL/kg/day.

The current invention further comprises a method for selecting an antibody (specifically) binding to at least one antigen with a systemic clearance (in cynomolgus monkeys) suitable to be used as therapeutic agent (in humans) comprising the following steps:

a) providing the antibody in different formats selected from the group consisting of
   i) a full length antibody, a CrossMab, a 2:1 heterodimeric T cell bispecific antibody, and any of the before fused to one, two, or three additional Fab, scFv, scFab, CrossFab molecules either directly or via a peptidic linker, and/or
   ii) a human IgG1 Fc-region, a human IgG1 Fc-region with the mutations L234A, L235A and P329G, a human IgG1 Fc-region with the knob-into-hole mutations, and combinations thereof,
b) performing an FcRn affinity chromatography with a positive linear pH gradient and a heparin affinity chromatography with a positive linear conductivity/salt gradient with each of the different antibody formats of a), and
c) selecting the antibody format
   i) if the relative retention time on the FcRn affinity chromatography column is less than 1.78 times the retention time difference between peaks 2 and 3 of a preparation of an oxidized anti-Her3 antibody of SEQ ID NO: 03 and 04, and
   ii) if the relative retention time on the heparin affinity chromatography column is less than 0.87 times the retention time of an anti-pTau antibody of SEQ ID NO: 01 and 02, and thereby selecting the antibody.

The current invention further comprises a method for selecting an antibody (specifically) binding to at least one antigen with a systemic clearance (in cynomolgus monkeys) suitable to be used as therapeutic agent (in humans) comprising the following steps:

a) providing at least two antibodies binding to the at least one antigen
   i) with different CDR sequences, or
   ii) with identical CDR sequences and different variable domain sequences, or
   iii) with identical CDR sequences in different antibody formats,
b) performing an FcRn affinity chromatography with a positive linear pH gradient and a heparin affinity chromatography with a positive linear conductivity/salt gradient with each of the different antibodies of a), and
c) selecting the antibody that has
   i) a relative retention time on the FcRn affinity chromatography column with respect to the retention time of a first reference antibody on the FcRn affinity chromatography column is less than a first threshold value, and
   ii) a ratio of the retention time on the heparin affinity chromatography column to the retention time of a second reference antibody on the heparin affinity chromatography column is less than a second threshold value.

In one embodiment the first reference antibody is an oxidized antibody preparation. In one embodiment the oxidized antibody preparation is a preparation comprising the antibody with respect to the methionine residues at position 252 in the heavy chain CH2 domains in non-oxidized form, in mono-oxidized form (only one of the two methionins at position 252 is oxidized) and in bi-oxidized form (both methionine residues at position 252 are oxidized) (numbering according to Kabat). In one embodiment the relative retention time is calculated based on the following formula $$t_{rel,i} = \frac{t_i - t_{reference\ antibody\ mono\text{-}oxidized\ peak}}{t_{reference\ antibody\ non\text{-}oxidized\ peak} - t_{reference\ antibody\ mono\text{-}oxidized\ peak}}$$

with $t_{rel,i}$=relative retention time of the antibody; $t_i$=retention time of the antibody. In one embodiment the first reference antibody is an anti-Her3 antibody that has a heavy chain with the amino acid sequence of SEQ ID NO: 03 and a light chain with the amino acid sequence of SEQ ID NO: 04. In one embodiment the first threshold value is 2. In one embodiment the first threshold value is 1.8. In one embodiment the first threshold value is 1.78.

In one embodiment the second reference antibody is an anti-pTau antibody that has a heavy chain with the amino acid sequence of SEQ ID NO: 01 and a light chain with the amino acid sequence of SEQ ID NO: 02. In one embodiment the second threshold value is 1. In one embodiment the second threshold value is 0.8. In one embodiment the second threshold value is 0.78.

In one embodiment step c) is selecting the antibody
   i) when/if the relative retention time on the FcRn affinity chromatography column is less than 1.78 times the retention time difference between peaks 2 and 3 of a preparation of an oxidized anti-Her3 antibody of SEQ ID NO: 03 and 04, and
   ii) when/if the relative retention time on the heparin affinity chromatography column is less than 0.87 times the retention time of an anti-pTau antibody of SEQ ID NO: 01 and 02.

In one embodiment the method further comprises the following step:

d) if none of the provided antibodies or antibody formats fulfills the criteria of step c) at least one further antibody format or antibody is provided and steps b) and c) are repeated.

The current invention comprises a method for producing an antibody comprising the following steps:

a) cultivating a mammalian cell expressing the antibody (comprising one or more nucleic acids encoding the antibody), and
b) recovering the antibody from the cell or the cultivation medium, wherein the antibody has been selected (from a multitude of antibodies and/or antibody formats) to have i) a relative retention time on an FcRn affinity chromatography column of less than 1.78 times the retention time difference between peaks 2 and 3 of a preparation of an oxidized anti-Her3 antibody of SEQ ID NO: 03 and 04, and ii) a relative retention time on a heparin affinity chromatography column of less than 0.87 times the retention time of an anti-pTau antibody of SEQ ID NO: 01 and 02.

The current invention comprises a method for selecting an antibody with a systemic clearance in cynomolgus monkeys of less than 8 mL/kg/day comprising the following steps:

a) optionally providing a sample comprising the antibody,
b) performing an FcRn affinity chromatography with a positive linear pH gradient and a heparin affinity chromatography with a positive linear conductivity/salt gradient, and
c) selecting the antibody
   i) if the relative retention time on the FcRn affinity chromatography column is less than 1.78 times the retention time difference between peaks 2 and 3 of a preparation of an oxidized anti-Her3 antibody of SEQ ID NO: 03 and 04, and
   ii) if the relative retention time on the heparin affinity chromatography column is less than 0.87 times the retention time of an anti-pTau antibody of SEQ ID NO: 01 and 02.

The current invention further comprises a method for producing an antibody comprising the following steps:

a) providing a cell comprising one or more nucleic acids encoding an antibody selected with a method according to the invention, and
b) cultivating the cell in a cultivation medium and recovering the antibody from the cell or the cultivation medium and thereby producing the antibody.

In one embodiment of all methods the relative retention time on the FcRn affinity chromatography column is calculated according to the following equation:

$$t_{rel,i} = \frac{t_i - t_{peak2}}{t_{peak3} - t_{peak2}}$$

based on the peak definition according to FIG. 1 ($t_{rel,i}$: relative retention time of peak i; $t_i$: retention time of peak i; $t_{peak2}$: retention time of peak 2 of the partially oxidized anti-Her3 antibody according to FIG. 1; $t_{peak}$: retention time of peak 3 of the anti-Her3 antibody according to FIG. 1).

In one embodiment of all methods the relative retention time on the heparin affinity chromatography column is calculated according to the following formula:

$$t_{rel,i} = \frac{t_i}{t_{pTau}}$$

($t_{rel,i}$: relative retention time of peak i; $t_i$: retention time of peak i; $t_{pTau}$: retention time of the anti-pTau antibody peak).

In one embodiment of all methods the antibody or antibody format is selected from the group consisting of a full length antibody comprising two antibody light chains and two antibody heavy chains, a CrossMab, a 2:1 heterodimeric T cell bispecific antibody, an antibody-cytokine fusion polypeptide, an Fc-region-cytokine fusion polypeptide, and an antibody-Fab fusion polypeptide.

In one embodiment of all methods the antibody comprises an Fc-region selected from the group consisting of a human IgG1 Fc-region, a human IgG1 Fc-region with the mutations L234A, L235A and P329G, a human IgG1 Fc-region with the knob-into-hole mutations, and combinations thereof.

In one embodiment in the FcRn affinity chromatography with a positive linear pH gradient is used an immobilized non-covalent complex of a neonatal Fc receptor (FcRn) and beta-2-microglobulin (b2m) as affinity chromatography ligand, wherein the non-covalent complex of a neonatal Fc receptor and beta-2-microglobulin is bound to a chromatography material and the non-covalent complex is conjugated to the solid phase via a specific binding pair, wherein the pH gradient is from a first pH value to a second pH value whereby the first pH value is from pH 3.5 to pH 6.4 and the second pH value is from pH 7.4 to pH 9.5, and wherein the non-covalent complex of a neonatal Fc receptor (FcRn) and beta-2-microglobulin (b2m) is mono-biotinylated and the solid phase is derivatized with streptavidin.

In one embodiment the pH gradient is from a first pH value to a second pH value whereby the first pH value is pH 5.5 and the second pH value is pH 8.8.

In one embodiment the beta-2-microglobulin is from the same species as the FcRn.

In one embodiment the FcRn is selected from human FcRn, cynomolgus FcRn, mouse FcRn, rat FcRn, sheep FcRn, dog FcRn, pig FcRn, minipig FcRn, and rabbit FcRn.

In one embodiment the beta-2-microglobulin is from the same species as the FcRn.

In one embodiment the beta-2-microglobulin is from a different species as the FcRn.

In one embodiment the antibody is a monoclonal antibody.

In one embodiment the antibody is a bispecific antibody.

In one embodiment the antibody is a chimeric antibody.

In general, the soluble extracellular domain of FcRn (SEQ ID NO: 31 for human FcRn) with C-terminal His-Avi Tag (SEQ ID NO: 32) was co-expressed with 132-microglobulin (SEQ ID NO: 33 for human beta-2-microglobulin) in mammalian cells. The non-covalent FcRn-microglobulin complex was biotinylated and loaded onto streptavidin derivatized sepharose.

In principle any buffer substance can be used in the methods as reported herein.

In one embodiment the reference antibody for the FcRn affinity chromatography is the anti-HER3 antibody with SEQ ID NO: 03 (heavy chain) and SEQ ID NO: 04 (light chain).

In one embodiment the reference antibody for the heparin affinity chromatography is the anti-pTau antibody with SEQ ID NO: 01 (heavy chain) and SEQ ID NO: 02 (light chain).

In one embodiment the antibody is a monospecific antibody or antibody fragment of fusion polypeptide, or a bispecific antibody or antibody fragment of fusion polypeptide, or a trispecific antibody or antibody fragment of fusion polypeptide, or a tetraspecific antibody or antibody fragment of fusion polypeptide.

In one embodiment the antibody is an antibody of the class IgG. In one embodiment the antibody is an antibody of the subclass IgG1, IgG2, IgG3 or IgG4. In one embodiment the antibody is an antibody of the subclass IgG1 or IgG4.

DETAILED DESCRIPTION OF THE INVENTION

The invention is based, at least in part, on the finding that the selection of antibodies with respect to/based on their clearance in cynomolgus single-dose pharmacokinetic (SDPK) studies can be improved by using a combination of FcRn and heparin affinity chromatography, compared to isolated (1-dimensional) FcRn or heparin chromatography, respectively. The improvement is amongst other things in the reduction of the number of deselected antibodies despite acceptable PK properties.

The invention is based, at least in part, on the finding that the combination of FcRn affinity chromatography and heparin affinity chromatography allows to define FcRn and heparin affinity chromatography column retention time thresholds and thereby a retention time region, wherein antibodies with slow clearance, i.e. long systemic circulation half-live, can be found. Thus, this combination allows amongst other things for an improved selection of antibodies with long systemic circulation half-live, for an improvement in the accuracy of pharmacokinetic prediction, and for a reduction of the number of antibodies deselected despite having a long systemic circulation half-live.

The invention is based, at least in part, on the finding that when the retention times on an FcRn affinity chromatography column and on a heparin affinity chromatography column are normalized based on the retention times of reference antibodies on the respective columns a relative retention time region comprising predominantly antibodies with slow clearance is defined. This region is defined by a relative retention time on the FcRn affinity chromatography column of less than 1.78 (with an anti-Her3 antibody as reference antibody) and by a relative retention time on the heparin affinity chromatography column of less than 0.87 (with an anti-pTau antibody as reference antibody).

I. Definitions

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

The knobs into holes dimerization modules and their use in antibody engineering are described in Carter P.; Ridgway J. B. B.; Presta L. G.: Immunotechnology, Volume 2, Number 1, February 1996, pp. 73-73(1).

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991).

Useful methods and techniques for carrying out the current invention are described in e.g. Ausubel, F. M. (ed.), Current Protocols in Molecular Biology, Volumes I to III (1997); Glover, N. D., and Hames, B. D., ed., DNA Cloning: A Practical Approach, Volumes I and II (1985), Oxford University Press; Freshney, R. I. (ed.), Animal Cell Culture—a practical approach, IRL Press Limited (1986); Watson, J. D., et al., Recombinant DNA, Second Edition, CHSL Press (1992); Winnacker, E. L., From Genes to Clones; N.Y., VCH Publishers (1987); Celis, J., ed., Cell Biology, Second Edition, Academic Press (1998); Freshney, R. I., Culture of Animal Cells: A Manual of Basic Technique, second edition, Alan R. Liss, Inc., N.Y. (1987).

The use of recombinant DNA technology enables the generation derivatives of a nucleic acid. Such derivatives can, for example, be modified in individual or several nucleotide positions by substitution, alteration, exchange, deletion or insertion. The modification or derivatization can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA; Hames, B. D., and Higgins, S. G., Nucleic acid hybridization—a practical approach (1985) IRL Press, Oxford, England).

It must be noted that as used herein and in the appended claims, the singular forms "a", "an", and "the" include plural reference unless the context clearly dictates otherwise. Thus, for example, reference to "a cell" includes one cell, a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

The term "determine" as used herein encompasses also the terms measure and analyze.

The term "comprising" also includes the term "consisting of".

The term "antibody" herein is used in a broad sense and encompasses various antibody structures, including but not limited to monoclonal full length antibodies and multispecific antibodies (e.g. bispecific antibodies, trispecific antibodies) so long as they have an Fc-region.

A "multispecific antibody" denotes an antibody that has binding specificities for at least two different epitopes on the same antigen or two different antigens. Multispecific antibodies can be prepared as full-length antibodies or antibody fragments (e.g. F(ab')2 bispecific antibodies) or combinations thereof (e.g. full length antibody plus additional scFv or Fab fragments). Engineered antibodies with two, three or more (e.g. four) functional antigen binding sites have also been reported (see, e.g., US 2002/0004587 A1).

The term "binding (to an antigen)" denotes the binding of an antibody in an in vitro assay. In one embodiment binding is determined in a binding assay in which the antibody is bound to a surface and binding of the antigen to the antibody is measured by Surface Plasmon Resonance (SPR). Binding means e.g. a binding affinity ($K_D$) of $10^{-8}$ M or less, in some embodiments of $10^{-13}$ to $10^{-8}$ M, in some embodiments of $10^{-13}$ to $10^{-9}$ M. The term "binding" also includes the term "specifically binding".

Binding can be investigated by a BIAcore assay (GE Healthcare Biosensor AB, Uppsala, Sweden). The affinity of the binding is defined by the terms $k_a$ (rate constant for the association of the antibody from the antibody/antigen complex), $k_d$ (dissociation constant), and $K_D$ ($k_d/k_a$).

The term "buffer substance" denotes a substance that when in solution can level changes of the pH value of the solution e.g. due to the addition or release of acidic or basic substances.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, β, ε, γ, and μ, respectively.

The term "Fc-fusion polypeptide" denotes a fusion of a binding domain (e.g. an antigen binding domain such as a single chain antibody, or a polypeptide such as a ligand of a receptor) with an antibody Fc-region.

The term "Fc-region of human origin" denotes the C-terminal region of an immunoglobulin heavy chain of human origin that contains at least a part of the hinge region, the CH2 domain and the CH3 domain. In one embodiment, a human IgG heavy chain Fc-region extends from Cys226, or from Pro230, to the carboxyl-terminus of the heavy chain. In one embodiment the Fc-region has the amino acid sequence of SEQ ID NO: 05. However, the C-terminal lysine (Lys447) of the Fc-region may or may not be present. The Fc-region is composed of two heavy chain Fc-region polypeptides, which can be covalently linked to each other via the hinge region cysteine residues forming inter-chain disulfide bonds.

The term "FcRn" denotes the human neonatal Fc-receptor. FcRn functions to salvage IgG from the lysosomal degradation pathway, resulting in reduced clearance and increased half-life. The FcRn is a heterodimeric protein consisting of two polypeptides: a 50 kDa class I major histocompatibility complex-like protein (α-FcRn) and a 15 kDa β2-microglobulin β2m). FcRn binds with high affinity to the CH2-CH3 portion of the Fc-region of IgG. The interaction between IgG and FcRn is strictly pH dependent and occurs in a 1:2 stoichiometry, with one IgG binding to two FcRn molecules via its two heavy chains (Huber, A. H., et al., J. Mol. Biol. 230 (1993) 1077-1083). FcRn binding occurs in the endosome at acidic pH (pH<6.5) and IgG is released at the neutral cell surface (pH of about 7.4). The pH-sensitive nature of the interaction facilitates the FcRn-mediated protection of IgGs pinocytosed into cells from intracellular degradation by binding to the receptor within the acidic environment of endosomes. FcRn then facilitates the recycling of IgG to the cell surface and subsequent release into the blood stream upon exposure of the FcRn-IgG complex to the neutral pH environment outside the cell.

The term "FcRn binding portion of an Fc-region" denotes the part of an antibody heavy chain polypeptide that extends approximately from EU position 243 to EU position 261 and approximately from EU position 275 to EU position 293 and approximately from EU position 302 to EU position 319 and approximately from EU position 336 to EU position 348 and approximately from EU position 367 to EU position 393 and EU position 408 and approximately from EU position 424 to EU position 440. In one embodiment one or more of the following amino acid residues according to the EU numbering of Kabat are altered F243, P244, P245, K246, P247, K248, D249, T250, L251, M252, I253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, I336, S337, K338, A339, K340, G341, Q342, P343, R344, E345, P346, Q347, V348, C367, V369, F372, Y373, P374, S375, D376, I377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440 (EU numbering).

The term "full length antibody" denotes an antibody having a structure substantially similar to a native antibody structure. A full length antibody comprises two full length antibody light chains comprising a light chain variable domain and a light chain constant domain and two full length antibody heavy chains comprising a heavy chain variable domain, a first constant domain, a hinge region, a second constant domain and a third constant domain. A full length antibody may comprise further domains, such as e.g. additional scFv or a scFab conjugated to one or more of the chains of the full length antibody. These conjugates are also encompassed by the term full length antibody.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "derived from" denotes that an amino acid sequence is derived from a parent amino acid sequence by introducing alterations at at least one position. Thus a derived amino acid sequence differs from the corresponding parent amino acid sequence at at least one corresponding position (numbering according to Kabat EU index for antibody Fc-regions). In one embodiment an amino acid sequence derived from a parent amino acid sequence differs by one to fifteen amino acid residues at corresponding positions. In one embodiment an amino acid sequence derived from a parent amino acid sequence differs by one to ten amino acid residues at corresponding positions. In one embodiment an amino acid sequence derived from a parent amino acid sequence differs by one to six amino acid residues at corresponding positions. Likewise, a derived amino acid sequence has a high amino acid sequence identity to its parent amino acid sequence. In one embodiment an amino acid sequence derived from a parent amino acid sequence has 80% or more amino acid sequence identity. In one embodiment an amino acid sequence derived from a parent amino acid sequence has 90% or more amino acid sequence identity. In one embodiment an amino acid sequence derived from a parent amino acid sequence has 95% or more amino acid sequence identity.

The term "human Fc-region polypeptide" denotes an amino acid sequence which is identical to a "native" or "wild-type" human Fc-region polypeptide. The term "variant (human) Fc-region polypeptide" denotes an amino acid sequence which derived from a "native" or "wild-type" human Fc-region polypeptide by virtue of at least one "amino acid alteration". A "human Fc-region" is consisting of two human Fc-region polypeptides. A "variant (human) Fc-region" is consisting of two Fc-region polypeptides, whereby both can be variant (human) Fc-region polypeptides or one is a human Fc-region polypeptide and the other is a variant (human) Fc-region polypeptide.

In one embodiment the human Fc-region polypeptide has the amino acid sequence of a human IgG1 Fc-region polypeptide of SEQ ID NO: 05, or of a human IgG2 Fc-region polypeptide of SEQ ID NO: 06, or of a human IgG3 Fc-region polypeptide of SEQ ID NO: 07, or of a human IgG4 Fc-region polypeptide of SEQ ID NO: 08. In one embodiment the Fc-region polypeptide is derived from an Fc-region polypeptide of SEQ ID NO: 05, or 06, or 07, or 08 and has at least one amino acid mutation compared to the Fc-region polypeptide of SEQ ID NO: 05, or 06, or 07, or 08. In one embodiment the Fc-region polypeptide comprises/has from about one to about ten amino acid mutations, and in one embodiment from about one to about five amino acid mutations. In one embodiment the Fc-region polypeptide has at least about 80% homology with a human Fc-region polypeptide of SEQ ID NO: 05, or 06, or 07, or 08. In one embodiment the Fc-region polypeptide has least about 90% homology with a human Fc-region polypeptide of SEQ ID NO: 05, or 06, or 07, or 08. In one embodiment the Fc-region polypeptide has at least about 95% homology with a human Fc-region polypeptide of SEQ ID NO: 05, or 06, or 07, or 08.

The Fc-region polypeptide derived from a human Fc-region polypeptide of SEQ ID NO: 05, or 06 or 07, or 08 is further defined by the amino acid alterations that are contained. Thus, for example, the term P329G denotes an Fc-region polypeptide derived human Fc-region polypeptide with the mutation of proline to glycine at amino acid position 329 relative to the human Fc-region polypeptide of SEQ ID NO: 05, or 06, or 07, or 08.

A human IgG1 Fc-region polypeptide has the following amino acid sequence:

```
                                            (SEQ ID NO: 05)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with the mutations L234A,

L235A has the following amino acid sequence:

```
                                            (SEQ ID NO: 09)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK
```

-continued

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with Y349C, T366S, L368A and Y407V mutations has the following amino acid sequence:

(SEQ ID NO: 10)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A human IgG1 Fc-region derived Fc-region polypeptide with S354C, T366W mutations has the following amino acid sequence:

(SEQ ID NO: 11)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with L234A, L235A mutations and Y349C, T366S, L368A, Y407V mutations has the following amino acid sequence:

(SEQ ID NO: 12)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A human IgG1 Fc-region derived Fc-region polypeptide with a L234A, L235A and S354C, T366W mutations has the following amino acid sequence:

(SEQ ID NO: 13)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with a P329G mutation has the following amino acid sequence:

(SEQ ID NO: 14)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with L234A, L235A mutations and P329G mutation has the following amino acid sequence:

(SEQ ID NO: 15)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with a P329G mutation and Y349C, T366S, L368A, Y407V mutations has the following amino acid sequence:

(SEQ ID NO: 16)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A human IgG1 Fc-region derived Fc-region polypeptide with a P329G mutation and S354C, T366W mutation has the following amino acid sequence:

(SEQ ID NO: 17)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with L234A, L235A, P329G and Y349C, T366S, L368A, Y407V mutations has the following amino acid sequence:

(SEQ ID NO: 18)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A human IgG1 Fc-region derived Fc-region polypeptide with L234A, L235A, P329G mutations and S354C, T366W mutations has the following amino acid sequence:

(SEQ ID NO: 19)
```
DKTHTCPPCPAPEAAGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALGAPIEKTISKAKGQPREPQVYTLPPCRDELTKNQVSLWCLVK
GFYPSDIAVEWESNGQPENNYKTTPPVLDSDGSFFLYSKLTVDKSRWQQG
NVFSCSVMHEALHNHYTQKSLSLSPGK.
```

A human IgG4 Fc-region polypeptide has the following amino acid sequence:

(SEQ ID NO: 08)
```
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK.
```

A human IgG4 Fc-region derived Fc-region polypeptide with S228P and L235E mutations has the following amino acid sequence:

(SEQ ID NO: 20)
```
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK.
```

A human IgG4 Fc-region derived Fc-region polypeptide with S228P, L235E mutations and P329G mutation has the following amino acid sequence:

(SEQ ID NO: 21)
```
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK.
```

A human IgG4 Fc-region derived Fc-region polypeptide with S354C, T366W mutations has the following amino acid sequence:

(SEQ ID NO: 22)
```
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPCQEEMTKNQVSLWCL
VKGFYPSDIAVEWESNGQPENNYKTTPPVLDSDGSFFLYSRLTVDKSRWQ
EGNVFSCSVMHEALHNHYTQKSLSLSLGK.
```

A human IgG4 Fc-region derived Fc-region polypeptide with Y349C, T366S, L368A, Y407V mutations has the following amino acid sequence:

(SEQ ID NO: 23)
```
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVCTLPPSQEEMTKNQVSLSCA
VKGFYPSDIAVEWESNGQPENNYKTTPPVLDSDGSFFLVSRLTVDKSRWQ
EGNVFSCSVMHEALHNHYTQKSLSLSLGK.
```

A human IgG4 Fc-region derived Fc-region polypeptide with a S228P, L235E and S354C, T366W mutations has the following amino acid sequence:

(SEQ ID NO: 24)
```
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPCQEEMTKNQVSLWCL
VKGFYPSDIAVEWESNGQPENNYKTTPPVLDSDGSFFLYSRLTVDKSRWQ
EGNVFSCSVMHEALHNHYTQKSLSLSLGK.
```

A human IgG4 Fc-region derived Fc-region polypeptide with a S228P, L235E and Y349C, T366S, L368A, Y407V mutations has the following amino acid sequence:

(SEQ ID NO: 25)
```
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVCTLPPSQEEMTKNQVSLSCA
VKGFYPSDIAVEWESNGQPENNYKTTPPVLDSDGSFFLVSRLTVDKSRWQ
EGNVFSCSVMHEALHNHYTQKSLSLSLGK.
```

A human IgG4 Fc-region derived Fc-region polypeptide with a P329G mutation has the following amino acid sequence:

(SEQ ID NO: 26)
```
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK.
```

A human IgG4 Fc-region derived Fc-region polypeptide with a P329G and Y349C, T366S, L368A, Y407V mutations has the following amino acid sequence:

(SEQ ID NO: 27)
```
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVCTLPPSQEEMTKNQVSLSCA
VKGFYPSDIAVEWESNGQPENNYKTTPPVLDSDGSFFLVSRLTVDKSRWQ
EGNVFSCSVMHEALHNHYTQKSLSLSLGK.
```

A human IgG4 Fc-region derived Fc-region polypeptide with a P329G and S354C, T366W mutations has the following amino acid sequence:

(SEQ ID NO: 28)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPCQEEMTKNQVSLWCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with a S228P, L235E, P329G and Y349C, T366S, L368A, Y407V mutations has the following amino acid sequence:

(SEQ ID NO: 29)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVCTLPPSQEEMTKNQVSLSCA

VKGFYPSDIAVEWESNGQPENNYKTTPPVLDSDGSFFLVSRLTVDKSRWQ

EGNVFSCSVMHEALHNHYTQKSLSLSLGK.

A human IgG4 Fc-region derived Fc-region polypeptide with a S228P, L235E, P329G and S354C, T366W mutations has the following amino acid sequence:

(SEQ ID NO: 30)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPCQEEMTKNQVSLWCL

VKGFYPSDIAVEWESNGQPENNYKTTPPVLDSDGSFFLYSRLTVDKSRWQ

EGNVFSCSVMHEALHNHYTQKSLSLSLGK.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., the CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., size exclusion chromatography or ion exchange or reverse phase HPLC). For review of methods for assessment of antibody purity, see, e.g., Flatman, S. et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "plasmid", as used herein, refers to a nucleic acid molecule capable of propagating another nucleic acid to which it is linked. The term includes the plasmid as a self-replicating nucleic acid structure as well as the plasmid incorporated into the genome of a host cell into which it has been introduced. Certain plasmids are capable of directing the expression of nucleic acids to which they are operatively linked. Such plasmids are referred to herein as "expression plasmid".

The term "positive linear pH gradient" denotes a pH gradient starting at a low (i.e. more acidic) pH value and ending at a higher (i.e. less acidic, neutral or alkaline) pH value. In one embodiment the positive linear pH gradient starts at a pH value of about 5.5 and ends at a pH value of about 8.8.

The term "recombinant antibody", as used herein, denotes all antibodies (chimeric, humanized and human) that are prepared, expressed, created or isolated by recombinant means. This includes antibodies isolated from a host cell such as a NSO, HEK, BHK or CHO cell or from an animal (e.g. a mouse) that is transgenic for human immunoglobulin genes or antibodies expressed using a recombinant expression plasmid transfected into a host cell. Such recombinant antibodies have variable and constant regions in a rearranged form. The recombinant antibodies as reported herein can be subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

A "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component of an assay is distinguished from inert solid surfaces in that a "solid support" contains at least one moiety on its surface, which is intended to interact chemically with a molecule. A solid phase may be a stationary component, such as a chip, tube, strip, cuvette, or microtiter plate, or may be non-stationary components, such as beads and microparticles. Microparticles can also be used as a solid support for homogeneous assay formats. A variety of microparticles that allow both non-covalent or covalent attachment of proteins and other substances may be used. Such particles include polymer particles such as polystyrene and poly (methylmethacrylate); gold particles such as gold nanoparticles and gold colloids; and ceramic particles such as silica, glass, and metal oxide particles. See for example Martin, C. R., et al., Analytical Chemistry-News & Features, May 1 (1998) 322A-327A, which is incorporated herein by reference. In one embodiment the solid support is sepharose.

The term "valent" as used within the current application denotes the presence of a specified number of binding sites in a (antibody) molecule. As such, the terms "bivalent", "tetravalent", and "hexavalent" denote the presence of two binding site, four binding sites, and six binding sites, respectively, in a (antibody) molecule. The bispecific antibodies as reported herein as reported herein are in one preferred embodiment "bivalent".

The term "variable region" or "variable domain" refer to the domain of an antibody heavy or light chain that is involved in binding of the antibody to its antigen. The variable domains of the heavy chain and light chain (VH and VL, respectively) of an antibody generally have similar structures, with each domain comprising four framework regions (FRs) and three hypervariable regions (HVRs) (see, e.g., Kindt, T. J. et al. Kuby Immunology, 6th ed., W. H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The terms "variant", "modified antibody", and "modified fusion polypeptide" denotes molecules which have an amino acid sequence that differs from the amino acid sequence of a parent molecule. Typically, such molecules have one or more alterations, insertions, or deletions. In one embodiment the modified antibody or the modified fusion polypeptide comprises an amino acid sequence comprising at least a portion of an Fc-region which is not naturally occurring. Such molecules have less than 100% sequence identity with the parent antibody or parent fusion polypeptide. In one embodiment the variant antibody or the variant fusion polypeptide has an amino acid sequence that has from about 75% to less than 100% amino acid sequence identity with the amino acid sequence of the parent antibody or parent fusion polypeptide, especially from about 80% to less than 100%, especially from about 85% to less than 100%, especially from about 90% to less than 100%, and especially from about 95% to less than 100%. In one embodiment the parent antibody or the parent fusion polypeptide and the variant antibody or the variant fusion polypeptide differ by one (a single), two or three amino acid residue(s).

II. Methods as Reported Herein

The clearances of antibodies with identical Fc-region span a wide range. Is there in influence of the respective Fv region, i.e. which biophysical properties differentiate fast cleared from slowly cleared antibodies.

Without being bound by this theory it is hypothesized that direct, charge-mediated interaction of Fv and FcRn impairs the release of the antibody from the FcRn at pH 7.4.

It has now been found that a combination of pinocytosis and FcRn binding evaluation can be used to predict/to more precisely evaluate the pharmacokinetics of an antibody. This has been realized by the combination of FcRn affinity chromatography (pH-gradient elution) and heparin affinity chromatography (salt-gradient elution).

An intravenous immunoglobulin (IVIG, a polyclonal mix of IgGs isolated from pooled human donor serum (>1000 donors)) was separated on a heparin affinity chromatography column giving rise to several broad peaks covering a wide retention time range. The same material showed a narrow elution peak on the FcRn column suggesting similar binding affinities for FcRn for the therein contained antibodies (see FIG. 4).

Heparin is a highly negatively charged glycosaminoglycan (polysaccharide) and a main component of the glycocalix covering endothelial cells.

The fraction with the highest (FIG. 4: 2) and the lowest (FIG. 4: 1) heparin retention time was tested in FcRn wild-type and FcRn knock-out mice. The observed clearance is shown in the following Table:

| clearance [mL/day/kg] | FcRn-wt mice | FcRn-knock-out mice |
|---|---|---|
| IVIG heparin fraction 1 | 4 | 32 |
| IVIG heparin fraction 2 | 5 | 76 |

Higher clearance was found for the strong heparin binder, indicating a higher pinocytosis rate, in both settings.

In the mouse model expressing murine FcRn, which has a significantly higher affinity to huIgG compared to endogenous mIgG, FcRn recycling dominates the pharmacokinetic (without being bound by this theory there is strongly reduced competition of endogenous mIgG with the injected huIgG compared to the scenario in a patient). In FcRn knockout mice FcRn recycling does not contribute to pharmacokinetics and every pinocytosis event leads to the degradation of the pinocytosed IgG. Therefore, the thereby determined clearance should be proportionate to the pinocytosis rate of the injected IgG sample, resulting in a significantly more pronounced clearance. These data correlate well with the prediction of the heparin column, thereby adding evidence to the validity of the heparin column as predictor for antibody pharmacokinetics via pinocytosis.

The following 35 antibodies having different formats and different specificities have been produced and analyzed with the methods as reported in the current examples:

| antibody no | format | Fc-region | antigen no. |
|---|---|---|---|
| 1 | IgG1, bivalent, monospecific, reference heparin | LALAPG | 1 |
| 2 | IgG1, bivalent, monospecific | wild-type | 2 |
| 3 | IgG1, bivalent, monospecific | wild-type | 3 |
| 4 | CrossMab, bivalent, bispecific | KiH | 4 + 5 |
| 5 | IgG1, bivalent, monospecific | wild-type | 6 |
| 6 | IgG1, bivalent, monospecific | wild-type | 7 |
| 7 | IgG1, bivalent, monospecific | wild-type | 8 |
| 8 | IgG1, bivalent, monospecific | wild-type | 9 |
| 9 | IgG1, bivalent, monospecific | wild-type | 10 |
| 10 | IgG1, bivalent, monospecific, reference FcRn | wild-type | 11 |
| 11 | IgG1, bivalent, monospecific | wild-type | 12 |
| 12 | IgG4, bivalent, monospecific | wild-type | 13 |
| 13 | IgG1, bivalent, monospecific | wild-type | 9 |
| 14 | IgG1, bivalent, monospecific | wild-type | 14 |
| 15 | IgG1, bivalent, monospecific | wild-type | 15 |
| 16 | Fc-region-cytokine fusion | LALAPG | 16 |
| 17 | 2:1 heterodimeric T cell bispecific | KiH | 17 + 18 |
| 18 | 2:1 heterodimeric T cell bispecific | KiH | 9 + 18 |
| 19 | IgG1, bivalent, monospecific - cytokine fusion | KiH LALAPG | 16 + 19 |
| 20 | IgG1, bivalent, monospecific - cytokine fusion | KiH LALAPG | 16 + 17 |
| 21 | IgG1, bivalent, monospecific | wild-type | 20 + 21 |
| 22 | IgG1, bivalent, monospecific | wild-type | 20 + 21 |
| 23 | IgG1, bivalent, monospecific | wild-type | 22 |
| 24 | IgG1, bivalent, monospecific | wild-type | 23 |
| 25 | IgG1, bivalent, monospecific | wild-type | 24 |
| 26 | IgG1, bivalent, monospecific | wild-type | 25 |
| 27 | IgG1, bivalent, monospecific | wild-type | 26 |
| 28 | IgG1, bivalent, monospecific | wild-type | 27 |
| 29 | IgG1, bivalent, monospecific | wild-type | 28 |
| 30 | 2:1 heterodimeric T cell bispecific | KiH LALAPG | 29 + 18 |
| 31 | IgG1, bivalent, monospecific | wild-type | 9 |
| 32 | 2:1 heterodimeric T cell bispecific | KiH LALAPG | 17 + 18 |
| 33 | IgG1, bivalent, monospecific | LALAPG | 9 |
| 34 | IgG1-Fab fusion, trivalent, bispecific | KiH LALAPG | 9 + 30 |
| 35 | IgG1, bivalent, monospecific | wild-type | 31 |

A bivalent, monospecific IgG1 antibody with a wild-type-Fc-region is an antibody comprising two antibody light chains (each comprising a light chain variable domain and a light chain constant domain) and two antibody heavy chains (each comprising a heavy chain variable domain, a hinge region and the heavy chain constant domains CH1, CH2 and CH3), whereby the Fc-region is a human IgG1 Fc-region, whereby the Fc-region C-terminal amino acid residues K or GK may be present or not independently of each other in the two antibody heavy chains. In one embodiment the human IgG1 Fc-region has the amino acid sequence of SEQ ID NO: 05.

A bivalent, bispecific IgG1 antibody with a KiH-Fc-region is an antibody comprising two antibody light chains (each comprising a light chain variable domain and a light chain constant domain) and two antibody heavy chains (each comprising a heavy chain variable domain, a hinge region and the heavy chain constant domains CH1, CH2 and CH3), whereby the Fc-region is a human IgG1 Fc-region, whereby the Fc-region C-terminal amino acid residues K or GK may be present or not independently of each other in the two antibody heavy chains, whereby one of the heavy chain comprises the hole mutations and the respective other heavy chain comprises the knob mutation. In one embodiment the heavy chain Fc-regions have the amino acid sequence of SEQ ID NO: 09 and 10, respectively.

The CH3 domains in the Fc-reign of the heavy chains of a bivalent bispecific antibody can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

The mutation T366W in the CH3 domain of an antibody heavy chain is denoted as "knob mutation" and the mutations T366S, L368A, Y407V in the CH3 domain of an antibody heavy chain are denoted as "hole mutations" (numbering according to Kabat EU index). An additional interchain disulfide bridge between the CH3 domains can also be used (Merchant, A. M., et al., Nature Biotech. 16 (1998) 677-681) e.g. by introducing a Y349C mutation into the CH3 domain of the heavy chain with the "knob mutation" and by introducing a E356C mutation or a S354C mutation into the CH3 domain of the heavy chain with the "hole mutations", or vice versa.

A bivalent, monospecific IgG1 antibody cytokine fusion with a KiH LALAPG-Fc-region is an antibody comprising two antibody light chains (each comprising a light chain variable domain and a light chain constant domain) and two antibody heavy chains (each comprising a heavy chain variable domain, a hinge region and the heavy chain constant domains CH1, CH2 and CH3), whereby the Fc-region is a human IgG1 Fc-region, whereby the Fc-region C-terminal amino acid residues K or GK may be present or not independently of each other in the two antibody heavy chains, whereby one of the heavy chains comprises the hole mutations and the respective other heavy chain comprises the knob mutation, whereby both heavy chains further comprise the amino acid mutations L234A, L235A and P329G. In one embodiment the heavy chain Fc-regions have the amino acid sequence of SEQ ID NO: 18 and 19, respectively.

A bivalent, bispecific CrossMab with a KiH-Fc-region is an antibody comprising a) a first light chain and a first heavy chain of an antibody specifically binding to a first antigen, and a second light chain and a second heavy chain of an antibody specifically binding to a second antigen, wherein the variable domains VL and VH of the second light chain and the second heavy chain are replaced by each other, or b) a first light chain and a first heavy chain of an antibody specifically binding to a first antigen, and a second light chain and a second heavy chain of an antibody specifically binding to a second antigen, wherein the constant domains CL and CH1 of the second light chain and the second heavy chain are replaced by each other, whereby the Fc-region is a human IgG1 Fc-region, whereby the Fc-region C-terminal amino acid residues K or GK may be present or not independently of each other in the two antibody heavy chains, whereby one of the heavy chains comprises the hole mutations and the respective other heavy chain comprises the knob mutation. In one embodiment the heavy chain Fc-regions have the amino acid sequence of SEQ ID NO: 09 and 10, respectively.

A 2:1 heterodimeric T cell bispecific antibody with a KiH-LALAPG-Fc-region is an antibody comprising a) a first Fab fragment which specifically binds to a first antigen;

b) a second Fab fragment which specifically binds to a second antigen, and wherein the variable domains VL and VH or the constant domains CL and CH1 of the Fab light chain and the Fab heavy chain are replaced by each other;

c) a third Fab fragment which specifically binds to the first antigen; and d) an Fc-region composed of a first and a second heavy chain Fc-region;

wherein (iii) the first Fab molecule under a) is fused at the C-terminus of the Fab heavy chain to the N-terminus of the Fab heavy chain of the second Fab molecule under b), and the second Fab molecule under b) and the third Fab molecule under c) are each fused at the C-terminus of the Fab heavy chain to the N-terminus of one of the heavy chain Fc-regions under d), whereby the Fc-region is a human IgG1 Fc-region, whereby the Fc-region C-terminal amino acid residues K or GK may be present or not independently of each other in the two antibody heavy chain Fc-regions, whereby one of the heavy chain Fc-regions comprises the hole mutations and the respective other heavy chain Fc-region comprises the knob mutation, whereby both heavy chain Fc-regions further comprise the amino acid mutations L234A, L235A and P329G. In one embodiment the heavy chain Fc-regions have the amino acid sequence of SEQ ID NO: 18 and 19, respectively.

A trivalent, bispecific IgG1-Fab fusion with KiH-LALAPG-Fc-region comprises a) two light chains and two heavy chains of an antibody, which specifically bind to a first antigen (and comprise two Fab fragments), b) one additional Fab fragment of an antibody, which specifically binds to a second antigen, wherein said additional Fab fragment is fused via a peptidic linker to the C-terminus of one of the heavy chains of a), wherein in the additional Fab fragment either the variable domains VL and VH are replaced by each other, and/or the constant domains CL and CH1 are replaced by each other, whereby the Fc-region is a human IgG1 Fc-region, whereby the Fc-region C-terminal amino acid residues K or GK may be present or not independently of each other in the two antibody heavy chains, whereby one of the heavy chains comprises the hole mutations and the respective other heavy chain comprises the knob mutation, whereby both heavy chains further comprise the amino acid mutations L234A, L235A and P329G. In one embodiment the heavy chain Fc-regions have the amino acid sequence of SEQ ID NO: 18 and 19, respectively.

An Fc-region-cytokine fusion with a LALAPG-Fc-region is an antibody Fc-region fusion comprising two antibody heavy chain Fc-region fragments (each comprising at least a fragment of a hinge region and the heavy chain constant domains CH1, CH2 and CH3), whereby the Fc-region is a human IgG1 Fc-region, whereby the Fc-region C-terminal amino acid residues K or GK may be present or not independently of each other in the two antibody heavy chain Fc-region fragments, whereby both antibody heavy chain Fc-region fragments comprise the amino acid mutations L234A, L235A and P329G. In one embodiment the heavy chain Fc-regions have the amino acid sequence of SEQ ID NO: 15.

In order to level intraday, intrapersonal and intra-laboratory variations the retention times have been normalized to a reference antibody on each of the affinity columns.

For the heparin affinity chromatography column, the anti-pTau antibody with heavy chains of SEQ ID NO: 01 and light chains of SEQ ID NO: 02 was chosen. This antibody shows a relatively long retention time on the heparin affinity chromatography column resulting in a robust relative retention time calculation.

For the FcRn affinity chromatography column a preparation comprising oxidized variants of the anti-Her 3 antibody with heavy chains of SEQ ID NO: 03 and light chains of SEQ ID NO: 04 was chosen. This antibody was chosen as it has a comparable AUC distribution as the antibody used in Stracke, J., et al. (mAbs 6 (2014) 1229-1242). For the 35 antibodies the retention times on an FcRn affinity chromatography column and a heparin affinity chromatography column have been determined. In addition single-dose pharmacokinetics have been determined in cynomolgus monkeys. The results are presented in the following Table (same antibody sequence as before).

| antibody no | heparin affinity column rel. retention (vs. pTau) | FcRn affinity column rel. retention (vs. Her3 Pre-peak 1 and Main Peak) | clearance* [mL/kg/day] |
|---|---|---|---|
| 1 | 1 | 0.9 | 61.1 |
| 2 | 1.01 | 3.92 | 5.01 |
| 3 | 0.72 | 0.61 | 3.34 |
| 4 | 0.59 | 0.88 | 3.97 |
| 5 | 0.67 | 0.36 | 3.47 |
| 6 | 0.61 | 0.59 | 5.13 |
| 7 | 0.64 | 0.22 | 6.41 |
| 8 | 0.56 | 2.52 | 4.1 |
| 9 | 0.66 | 0.4 | 5.28 |
| 10 | 0.66 | 1.03 | 4.1 |
| 11 | 0.67 | 0.43 | 5.52 |
| 12 | 0.63 | −0.22 | 1.6 |
| 13 | 0.65 | 1.21 | <8 |
| 14 | 0.44 | 0.29 | 4.73 |
| 15 | 0.26 | −0.46 | 2.4 |
| 16 | 1.05 | 0.52 | >12 |
| 17 | 1 | 1.42 | 24.9 |
| 18 | 0.8 | 3.29 | 90 |
| 19 | 0.99 | 0.78 | 17 |
| 20 | 1.09 | 1.39 | 16.4 |
| 21 | 0.9 | 3.36 | >8 |
| 22 | 0.66 | 0.39 | >8 |
| 23 | 0.53 | 0.61 | 5.37 |
| 24 | 0.13 | −0.199 | 2.5 |
| 25 | 1.01 | 1.78 | 8.16 |
| 26 | 0.26 | −0.16 | 4.81 |
| 27 | 0.53 | 0.37 | 2.45 |
| 28 | 0.59 | 0.17 | 4.8 |
| 29 | 0.52 | 2.43 | 4.87 |
| 30 | 0.79 | 0.58 | 6.3 |
| 31 | 0.55 | 2.24 | 31.92 |
| 32 | 0.77 | 0.42 | 7.5 |
| 33 | 0.52 | 1.91 | 10.08 |
| 34 | 0.55 | 1.86 | 31.92 |
| 35 | 0.84 | 0.01 | 4.63 |

The clearance is ranked as follows:

fast: >12 mL/kg/day;

borderline: 8-12 mL/kg/day;

acceptable: 2.5≤X<8 mL/kg/day;

very good: <2.5 mL/kg/day.

In the following Table it is shown that based on the individual, isolated results of the two affinity chromatographies the antibodies in brackets would have been deselected; based on the pharmacokinetic determination the antibodies in brackets in the column “clearance” would have been deselected.

| heparin affinity column rel. retention (vs. pTau) | FcRn affinity column rel. retention (vs. Her3 Pre-peak 1 and Main Peak) | clearance |
|---|---|---|
| (1) | 1 | (1) |
| (2) | (2) | 2 |
| 3 | 3 | 3 |
| 4 | 4 | 4 |
| 5 | 5 | 5 |
| 6 | 6 | 6 |
| 7 | 7 | 7 |
| 8 | (8) | 8 |
| 9 | 9 | 9 |
| 10 | 10 | 10 |
| 11 | 11 | 11 |
| 12 | 12 | 12 |
| 13 | 13 | 13 |
| 14 | 14 | 14 |
| 15 | 15 | 15 |
| (16) | 16 | (16) |
| (17) | 17 | (17) |
| 18 | (18) | (18) |
| (19) | 19 | (19) |
| (20) | 20 | (20) |
| (21) | (21) | (21) |
| 22 | 22 | (22) |
| 23 | 23 | 23 |
| 24 | 24 | 24 |
| (25) | 25 | (25) |
| 26 | 26 | 26 |
| 27 | 27 | 27 |
| 28 | 28 | 28 |
| 29 | (29) | 29 |
| 30 | 30 | 30 |
| 31 | (31) | (31) |
| 32 | 32 | 32 |
| 33 | (33) | (33) |
| 34 | (34) | (34) |
| 35 | 35 | 35 |

In the following Tables the results are given based on the relative retention times on the respective columns. Deselected antibodies are shown in brackets.

| antibody no | heparin affinity column rel. retention (vs. pTau) | clearance* [mL/kg/day] |
|---|---|---|
| 20 | (1.09) | (16.4) |
| 16 | (1.05) | (>12) |
| 25 | (1.01) | (8.16) |
| 2 | (1.01) | 5.01 |
| 1 | (1) | (61.1) |
| 17 | (1) | (24.9) |
| 19 | (0.99) | (17) |
| 21 | (0.9) | (>8) |
| 35 | 0.84 | 4.63 |
| 18 | 0.8 | (90) |
| 30 | 0.79 | 6.3 |
| 32 | 0.77 | 7.5 |
| 3 | 0.72 | 3.34 |
| 11 | 0.67 | 5.52 |
| 5 | 0.67 | 3.47 |
| 22 | 0.66 | (>8) |
| 9 | 0.66 | 5.28 |
| 10 | 0.66 | 4.1 |
| 13 | 0.65 | <8 |
| 7 | 0.64 | 6.41 |
| 12 | 0.63 | 1.6 |
| 6 | 0.61 | 5.13 |
| 28 | 0.59 | 4.8 |
| 4 | 0.59 | 3.97 |
| 8 | 0.56 | 4.1 |
| 31 | 0.55 | (31.92) |
| 34 | 0.55 | (31.92) |
| 23 | 0.53 | 5.37 |
| 27 | 0.53 | 2.45 |
| 33 | 0.52 | (10.08) |
| 29 | 0.52 | 4.87 |
| 14 | 0.44 | 4.73 |
| 26 | 0.26 | 4.81 |
| 15 | 0.26 | 2.4 |
| 24 | 0.13 | 2.5 |

| antibody no | FcRn affinity column rel. retention (vs. Her3 Pre-peak 1 and Main Peak) | clearance* [mL/kg/day] |
|---|---|---|
| 2 | (3.92) | 5.01 |
| 21 | (3.36) | (>8) |
| 18 | (3.29) | 90 |
| 8 | (2.52) | 4.1 |
| 29 | (2.43) | 4.87 |
| 31 | (2.24) | (31.92) |
| 33 | (1.91) | (10.08) |
| 34 | (1.86) | (31.92) |
| 25 | (1.78) | (8.16) |
| 17 | 1.42 | (24.9) |
| 20 | 1.39 | (16.4) |
| 13 | 1.21 | <8 |
| 10 | 1.03 | 4.1 |
| 1 | 0.9 | (61.1) |
| 4 | 0.88 | 3.97 |
| 19 | 0.78 | (17) |
| 23 | 0.61 | 5.37 |
| 3 | 0.61 | 3.34 |
| 6 | 0.59 | 5.13 |
| 30 | 0.58 | 6.3 |
| 16 | 0.52 | (>12) |
| 11 | 0.43 | 5.52 |
| 32 | 0.42 | 7.5 |
| 9 | 0.4 | 5.28 |
| 22 | 0.39 | (>8) |
| 27 | 0.37 | 2.45 |
| 5 | 0.36 | 3.47 |
| 14 | 0.29 | 4.73 |
| 7 | 0.22 | 6.41 |
| 28 | 0.17 | 4.8 |
| 35 | 0.01 | 4.63 |
| 24 | −0.199 | 2.5 |
| 12 | −0.22 | 1.6 |
| 15 | −0.46 | 2.4 |
| 26 | −0.16 | 4.81 |

The correlation of retention times and pharmacokinetic behavior is shown in FIG. 2. It can be seen that a hitherto unknown correlation between relative retention times on the two affinity chromatography columns and pharmacokinetic behavior is existing. It has been found that a region comprising predominantly antibodies with slow clearance is defined by a relative retention time on the FcRn affinity chromatography column of less than 1.78 (with an anti-Her3 antibody as reference antibody) and by a relative retention time on the heparin affinity chromatography column of less than 0.87 (with an anti-pTau antibody as reference antibody). The respective correlation with the threshold values marked is shown in FIG. 3.

In the following table the antibodies deselected (in brackets) by the four methods, respectively, are shown: based on the isolated heparin affinity chromatography (column 1), based on the isolated FcRn affinity chromatography (column 2), based on the SDPK clearance (column 3) and based on the correlated retention times on two orthogonal affinity columns in the inventive method as reported herein.

| column 1 heparin affinity column rel. retention (vs. pTau) | column 2 FcRn affinity column rel. retention (vs. Her3 Pre-peak 1 and Main Peak) | column 3 clearance | column 4 heparin + FcRn rel. retention times |
|---|---|---|---|
| (1) | 1 | (1) | (1) |
| (2) | (2) | 2 | (2) |
| 3 | 3 | 3 | 3 |
| 4 | 4 | 4 | 4 |
| 5 | 5 | 5 | 5 |
| 6 | 6 | 6 | 6 |
| 7 | 7 | 7 | 7 |
| 8 | (8) | 8 | (8) |
| 9 | 9 | 9 | 9 |
| 10 | 10 | 10 | 10 |
| 11 | 11 | 11 | 11 |
| 12 | 12 | 12 | 12 |
| 13 | 13 | 13 | 13 |
| 14 | 14 | 14 | 14 |
| 15 | 15 | 15 | 15 |
| (16) | 16 | (16) | (16) |
| (17) | 17 | (17) | (17) |
| 18 | (18) | (18) | (18) |
| (19) | 19 | (19) | (19) |
| (20) | 20 | (20) | (20) |
| (21) | (21) | (21) | (21) |
| 22 | 22 | (22) | 22 |
| 23 | 23 | 23 | 23 |
| 24 | 24 | 24 | 24 |
| (25) | 25 | (25) | (25) |
| 26 | 26 | 26 | 26 |
| 27 | 27 | 27 | 27 |
| 28 | 28 | 28 | 28 |
| 29 | (29) | 29 | (29) |
| 30 | 30 | 30 | 30 |
| 31 | (31) | (31) | (31) |
| 32 | 32 | 32 | 32 |
| 33 | (33) | (33) | (33) |
| 34 | (34) | (34) | (34) |
| 35 | 35 | 35 | 35 |
| false prediction (deselected despite having suitable clearance + not deselected although having non-suitable clearance): | | | |
| 6 | 10 | 0 (reference) | 4 |

Thus, with the method according to the current invention an improved selection of antibodies with long systemic circulation half-live, an improvement in the accuracy of pharmacokinetic prediction, and a reduction of the number of antibodies deselected despite having a long systemic circulation half-live can be achieved.

When using a baculovirus based assay known from the art only about 50% of the antibodies are predicted correctly.

Thus, the method according to the invention can be used to identify antibodies, including Fc-region fusion polypeptides, with good pharmacokinetic properties without the need to perform animal pharmacokinetic studies.

Thus, the current invention comprises a method for selecting an antibody with a systemic clearance (in cynomolgus monkeys) suitable to be used as therapeutic agent (in humans) comprising the following steps:

a) optionally providing a sample comprising the antibody,
b) performing an FcRn affinity chromatography with a positive linear pH gradient and a heparin affinity chromatography with a positive linear conductivity/salt gradient, and
c) selecting the antibody
   i) if the relative retention time of the antibody on the FcRn affinity chromatography column with respect to the retention time of a first reference antibody on the FcRn affinity chromatography column is less than a first threshold value, and
   ii) if the ratio of the retention time of the antibody on the heparin affinity chromatography column to the retention time of a second reference antibody on the heparin affinity chromatography column is less than a second threshold value.

The current invention further comprises a method for selecting an antibody (specifically) binding to at least one antigen with a systemic clearance (in cynomolgus monkeys) suitable to be used as therapeutic agent (in humans) comprising the following steps:

a) providing the antibody in different formats,
b) performing an FcRn affinity chromatography with a positive linear pH gradient and a heparin affinity chromatography with a positive linear conductivity/salt gradient with each of the different antibody formats of a), and
c) selecting the antibody format that has
   i) a relative retention time on the FcRn affinity chromatography column with respect to the retention time of a first reference antibody on the FcRn affinity chromatography column is less than a first threshold value, and
   ii) a ratio of the retention time on the heparin affinity chromatography column to the retention time of a second reference antibody on the heparin affinity chromatography column is less than a second threshold value.

The current invention further comprises a method for selecting an antibody (specifically) binding to at least one antigen with a systemic clearance (in cynomolgus monkeys) suitable to be used as therapeutic agent (in humans) comprising the following steps:

a) providing at least two antibodies binding to the at least one antigen
   i) with different CDR sequences, or
   ii) with identical CDR sequences and different variable domain sequences, or
   iii) with identical CDR sequences in different formats,
b) performing an FcRn affinity chromatography with a positive linear pH gradient and a heparin affinity chromatography with a positive linear conductivity/salt gradient with each of the different antibodies of a), and
c) selecting the antibody that has
   i) a relative retention time on the FcRn affinity chromatography column with respect to the retention time of a first reference antibody on the FcRn affinity chromatography column is less than a first threshold value, and
   ii) a ratio of the retention time on the heparin affinity chromatography column to the retention time of a second reference antibody on the heparin affinity chromatography column is less than a second threshold value.

In one embodiment the first reference antibody is an oxidized antibody preparation. In one embodiment the oxidized antibody preparation is a preparation comprising the antibody with respect to the methionine residues at position 252 in the heavy chain CH2 domains in non-oxidized form, in mono-oxidized form (only one of the two methionins at position 252 is oxidized) and in bi-oxidized form (both methionine residues at position 252 are oxidized) (numbering according to Kabat). In one embodiment the relative retention time is calculated based on the following formula $$t_{rel,i} = \frac{t_i - t_{reference\ antibody\ mono\text{-}oxidized\ peak}}{t_{reference\ antibody\ non\text{-}oxidized\ peak} - t_{reference\ antibody\ mono\text{-}oxidized\ peak}}$$

with $t_{rel,i}$=relative retention time of the antibody; $t_i$=retention time of the antibody. In one embodiment the first reference antibody is an anti-Her3 antibody that has a heavy chain with the amino acid sequence of SEQ ID NO: 03 and a light chain with the amino acid sequence of SEQ ID NO: 04. In one embodiment the first threshold value is 2. In one embodiment the first threshold value is 1.8. In one embodiment the first threshold value is 1.78.

In one embodiment the second reference antibody is an anti-pTau antibody that has a heavy chain with the amino acid sequence of SEQ ID NO: 01 and a light chain with the amino acid sequence of SEQ ID NO: 02. In one embodiment the second threshold value is 1. In one embodiment the second threshold value is 0.8. In one embodiment the second threshold value is 0.78.

In one embodiment a systematic clearance in cynomolgus monkey suitable for therapeutic application (in humans), i.e. the antibodies can be used as therapeutic agent, is 8 mL/kg/day or less. In one embodiment the systematic clearance is less than 8 mL/kg/day. In one embodiment the systematic clearance is less than 6 mL/kg/day.

In one embodiment the method for selecting an antibody with a systemic clearance in cynomolgus monkeys of less than 8 mL/kg/day comprises the following steps:

a) optionally providing a sample comprising the antibody,
b) performing an FcRn affinity chromatography with a positive linear pH gradient and a heparin affinity chromatography with a positive linear conductivity/salt gradient, and
c) selecting the antibody
   i) if the relative retention time on the FcRn affinity chromatography column is less than 1.78 times the retention time difference between peaks 2 and 3 of a preparation of an oxidized anti-Her3 antibody of SEQ ID NO: 03 and 04, and
   ii) if the relative retention time on the heparin affinity chromatography column is less than 0.87 times the retention time of an anti-pTau antibody of SEQ ID NO: 01 and 02.

In one embodiment the relative retention time in step c) i) is calculated according to the following equation:

$$t_{rel,i} = \frac{t_i - t_{peak2}}{t_{peak3} - t_{peak2}}$$

based on the peak definition according to FIG. 1 ($t_{rel,i}$: relative retention time of peak i; $t_i$: retention time of peak i; $t_{peak2}$: retention time of peak 2 of the partially oxidized anti-Her3 antibody according to FIG. 1; $t_{peak}$3: retention time of peak 3 of the anti-Her3 antibody according to FIG. 1).

In one embodiment the relative retention time in step c) ii) is calculated according to the following formula:

$$t_{rel,i} = \frac{t_i}{t_{pTau}}$$

($t_{rel,i}$: relative retention time of peak i; $t_i$: retention time of peak i; $t_{pTau}$: retention time of the anti-pTau antibody peak).

In one embodiment an immobilized non-covalent complex of a neonatal Fc receptor (FcRn) and beta-2-microglobulin (b2m) is used as affinity chromatography ligand in the FcRn affinity chromatography with a positive linear pH gradient, wherein the non-covalent complex of a neonatal Fc receptor and beta-2-microglobulin is bound to a chromatography material and the non-covalent complex is conjugated to the solid phase via a specific binding pair, wherein the pH gradient is from a first pH value to a second pH value whereby the first pH value is from pH 3.5 to pH 6.4 and the second pH value is from pH 7.4 to pH 9.5, and wherein the non-covalent complex of a neonatal Fc receptor (FcRn) and beta-2-microglobulin (b2m) is mono-biotinylated and the solid phase is derivatized with streptavidin.

In one embodiment the pH gradient is from a first pH value to a second pH value whereby the first pH value is pH 5.5 and the second pH value is pH 8.8.

In one embodiment the antibody is binding to two antigens.

In one embodiment the method further comprises the step:

d) if none of the provided antibodies or antibody formats fulfills the criteria of step c) at least one further antibody format or antibody is provided and steps b) and c) are repeated.

In one embodiment the FcRn affinity chromatography is performed with an FcRn affinity chromatography column comprising streptavidin sepharose conjugated to FcRn beta-2-microglobulin complex (3 mg complex/1 ml of sepharose) and that has a length of about 50 mm and internal diameter of about 4.6 mm. In one embodiment the FcRn affinity chromatography is performed as follows: i) 30 μg of sample is applied onto the FcRn affinity column equilibrated with 20 mM MES buffer supplemented with 140 mM NaCl, adjusted to pH 5.5; ii) washing the column for 10 minutes with a buffer comprising (v/v) 80% 20 mM MES buffer supplemented with 140 mM NaCl, adjusted to pH 5.5 and 20% 20 mM Tris/HCl, with 140 mM NaCl, adjusted to pH 8.8 at a flow rate of 0.5 mL/min; iii) eluting and measuring the retention time with a linear gradient from the buffer of step ii) to a buffer comprising (v/v) 30% 20 mM MES buffer supplemented with 140 mM NaCl, adjusted to pH 5.5 and 70% 20 mM Tris/HCl, with 140 mM NaCl, adjusted to pH 8.8 at a flow rate of 0.5 mL/min.

In one embodiment the oxidized anti-Her3 antibody preparation is obtained by incubation of the anti-Her3 antibody for 18 hours at room temperature with 0.02% hydrogen peroxide solution.

In one embodiment the heparin affinity chromatography is performed with a heparin affinity chromatography column comprising heparin conjugated to sulfated glycosaminoglycan on a hydroxylated methacrylic polymer and that has a length of about 50 mm and in internal diameter of about 5 mm. In one embodiment the heparin affinity chromatography is performed as follows: i) applying 20 to 50 μg of protein samples in low-salt buffer (≤25 mM ionic strength) to a heparin affinity chromatography column pre-equilibrated with 50 mM TRIS buffer adjusted to pH 7.4 at room temperature; ii) eluting with a linear gradient from 0-100% 50 mM TRIS buffer supplemented with 1000 mM NaCl and adjusted to pH 7.4 over 32 minutes at a flow rate of 0.8 mg/mL.

In one embodiment the beta-2-microglobulin is from the same species as the FcRn.

The herein used FcRn affinity chromatography column comprises a matrix and matrix bound chromatographical functional groups, wherein the matrix bound chromatographical functional group comprises a non-covalent complex of neonatal Fc receptor (FcRn) and beta-2-microglobulin.

In one embodiment herein the FcRn is selected from human FcRn, cynomolgus FcRn, mouse FcRn, rat FcRn, sheep FcRn, dog FcRn, pig FcRn, minipig FcRn, and rabbit FcRn.

In one embodiment the beta-2-microglobulin is from the same species as the FcRn.

In one embodiment the beta-2-microglobulin is from a different species as the FcRn.

In one embodiment the antibody is selected from the group consisting of a full length antibody, a CrossMab, a 2:1 heterodimeric T cell bispecific antibody, an antibody-cytokine fusion polypeptide, an Fc-region-cytokine fusion polypeptide, and an antibody-Fab fusion polypeptide.

In one embodiment the antibody comprises an Fc-region selected from the group consisting of a human IgG1 Fc-region, a human IgG1 Fc-region with the mutations L234A, L235A and P329G, a human IgG1 Fc-region with the knob-into-hole mutations, and combinations thereof.

In one embodiment the antibody format is selected from the group consisting of a full length antibody, a CrossMab, a 2:1 heterodimeric T cell bispecific antibody, and any of the before fused to one, two, or three additional Fab, scFv, scFab, CrossFab molecules either directly or via a peptidic linker.

In one embodiment the antibody format comprises an Fc-region selected from the group consisting of a human IgG1 Fc-region, a human IgG1 Fc-region with the mutations L234A, L235A and P329G, a human IgG1 Fc-region with the knob-into-hole mutations, and combinations thereof.

In one embodiment the antibody is a monoclonal antibody.

In one embodiment the antibody is a bispecific antibody.

In one embodiment the antibody is a chimeric antibody.

In general, the soluble extracellular domain of FcRn (SEQ ID NO: 31 for human FcRn) with C-terminal His-Avi Tag (SEQ ID NO: 32) was co-expressed with $\beta_2$-microglobulin (SEQ ID NO: 33 for human beta-2-microglobulin) in mammalian cells. The non-covalent FcRn-microglobulin complex was biotinylated and loaded onto streptavidin derivatized sepharose.

In principle any buffer substance can be used in the methods as reported herein.

To further elucidate the relation of charge and heparin/FcRn-binding and thereby pharmacokinetics, variants of antibody no. 5 were synthesized covering the biophysical space of charges and hydrophobicities normally seen in antibody Fvs.

Variants carrying positively charged patches showed strong heparin and FcRn column retention (relative retention of the FcRn column of 0.5 and more and relative retention on the heparin column of 0.8 or more), which predicts fast clearance.

Variants carrying negatively charged patches showed weak heparin and FcRn column retention (relative retention of the FcRn column of 0.25 and less and relative retention on the heparin column of 0.6 or less), which predicts slow clearance.

When combining negatively and positively charged patches, the resulting antibody variant behaves as if it was carrying only positively charged patches.

For the wild-type antibody no. 5 and four variants thereof the clearance in FcRn knock-out mice was determined (FIG. 5 and FIG. 6). All three tested variants carrying positively charged patches show very high clearance compared to the wild-type antibody no. 5 in FcRn knock-out mice, correlating well with the column retentions. The variant carrying a negatively charged patch shows significantly reduced clearance in this mouse model also correlating well with the column retentions.

In order to determine the effect of "patchiness" on clearance (i.e. the effect of the concentration of surface charges to form a charge patch in contrast to an even charge distribution) five variants of antibody no. 5 were generated wherein the total number of positive and negative charges remained unchanged while the distribution of the charges on the Fab surface was incrementally changed from "even" to "patchy".

Although, both positive and negative charged patches were created, the heparin column retention increased with increasing patchiness. This indicates a bigger or even dominant effect of the positively charged patches compared to the negatively charged ones as already seen above. The calculated pI of these variants is nearly unchanged while the clearance in FcRn knock-out mice of the patchiest variant is significantly higher than that with the most even charge distribution (almost doubled; FIG. 7). These data suggest, without being bound by this theory, that "patchiness" or rather the influence of positively charged patches determines clearance in comparison to the pI which is a rather broad and therefore poor predictor of pharmacokinetics.

In order to determine the effect of replacing the permanently positively charged amino acids lysine and arginine with pH-dependently charged histidine a variant of antibody no. 5 in which all HC Fv positively charged amino acid residues were replaced with histidines (7 changes in total) was generated. This was compared by the heparin and FcRn column relative retention times and in vivo pharmacokinetic with the wild-type antibody no. 5.

Without being bound by this theory it is assumed that in blood serum at neutral pH, the charge of histidine is mostly neutral, therefore reducing binding to the negatively charged glycocalix and subsequently the pinocytosis rate. Within the acidic endosome histidine is mostly positive charged and therefore contributes to the binding to FcRn via Fv-FcRn avidity. Being recycled, the histidine mutated IgG is brought to the cell surface where efficient dissociation from FcRn is required for good pharmacokinetic. Histidines that are now exposed to the neutral pH of the serum become deprotonated and therefore weaken the avidity interaction with FcRn allowing for improved release to the serum.

It has been found that the histidine mutant showed reduced heparin retention, whereas FcRn retention remains mostly unaltered (FIG. 8). Without being bound by this theory, this reflects the pH-dependency.

In vivo, clearance of the histidine mutant is significantly reduced compared to wild-type antibody in the FcRn knock-out mouse (FIG. 9 and FIG. 10).

The current invention further comprises a method for selecting a variant antibody of a parent antibody, which is (specifically) binding to the same antigen as the parent antibody, which has a systemic clearance that is different from the systematic clearance of the parent antibody, and which is suitable as therapeutic agent (in humans) based on its pharmacokinetic properties, comprising the following steps:

a) providing at least one variant antibody of a parent antibody in which the charge distribution in the Fv fragment has been changed by
   i) changing at least one (permanently) negatively charged or not charged amino acid residue to a (permanently) positively charged amino acid residue, or
   ii) changing at least one (permanently) positively charged or not charged amino acid residue to a (permanently) negatively charged amino acid residue, or
   iii) changing at least one (permanently) charged amino acid residue to an amino acid residue with the opposite charge, or
   iv) changing at least one permanently charged amino acid residue to a pH-dependently charged amino acid residue, or
   v) a combination of i) to iv),
b) selecting the variant antibody that has a systemic clearance that is different from the systematic clearance of the parent antibody and that is suitable as therapeutic agent (in humans).

In one embodiment the method comprises the following additional steps:

b) performing an FcRn affinity chromatography with a positive linear pH gradient and a heparin affinity chromatography with a positive linear conductivity/salt gradient with the parent antibody and the at least one variant antibody, and
c) selecting the variant antibody that has
   i) a relative retention time on the FcRn affinity chromatography column that is less than the retention time of the parent antibody on the (same) FcRn affinity chromatography column (under the same elution conditions), or
   ii) a relative retention time on the heparin affinity chromatography column that is less than the retention time of the parent antibody on the (same) heparin affinity chromatography column (under the same elution conditions), or
   iii) both of i) and ii).

In one embodiment the method comprises the following additional steps:

b) performing an FcRn affinity chromatography with a positive linear pH gradient and a heparin affinity chromatography with a positive linear conductivity/salt gradient with the parent antibody and the at least one variant antibody, and
c) selecting the variant antibody that has
   i) a relative retention time on the FcRn affinity chromatography column that is more than the retention time of the parent antibody on the (same) FcRn affinity chromatography column (under the same elution conditions), or
   ii) a relative retention time on the heparin affinity chromatography column that is more than the retention time of the parent antibody on the (same) heparin affinity chromatography column (under the same elution conditions), or
   iii) both of i) and ii).

In one embodiment the method comprises the following additional steps:

b) performing an FcRn affinity chromatography with a positive linear pH gradient and a heparin affinity chromatography with a positive linear conductivity/salt gradient with the parent antibody and the at least one variant antibody, and
c) selecting the variant antibody that has
   i) a relative retention time on the FcRn affinity chromatography column that is less or more than the retention time of the parent antibody on the (same) FcRn affinity chromatography column (under the same elution conditions), or
   ii) a relative retention time on the heparin affinity chromatography column that is less or more than the retention time of the parent antibody on the (same) heparin affinity chromatography column (under the same elution conditions), or
   iii) both of i) and ii), wherein in i) the relative retention time is less and ii) it is more, or vice versa.

In one embodiment the variant antibody has at least one additional negatively charged patch on its (solvent-exposed) surface.

To determine charged patches on the (solvent exposed) surface of an antibody different methods and tools are known to a person skilled in the art. There are tools provided by different vendors or academic groups. For example, herein an in-silico calculation method based on the X-ray structure or a homology model, followed by pH-protonation of acidic and basic amino acid side-chains and calculation of the 3D charge distribution using the software CHARMM and Delphi as implemented in the software suite Discovery Studio (vendor: Dassault Systems) was used.

In one embodiment the variant antibody has at least one additional positively charged patch on its (solvent-exposed) surface.

In one embodiment the variant antibody has the same (surface) net charge as the parent antibody.

In one embodiment a (permanently) negatively charged amino acid residue is selected from the group consisting of glutamate and aspartate.

In one embodiment a (permanently) positively charged amino acid residue is selected from the group consisting of arginine and lysine.

In one embodiment the pH-dependently charged amino acid residue is histidine.

In one embodiment a permanently charged amino acid residue has the same (net) charge in the pH range from pH 6 to pH 8.

In one embodiment a pH-dependently charged amino acid residue has a first (net) charge at pH 6 and an opposite second (net) charge at pH 8.

Figure 1:
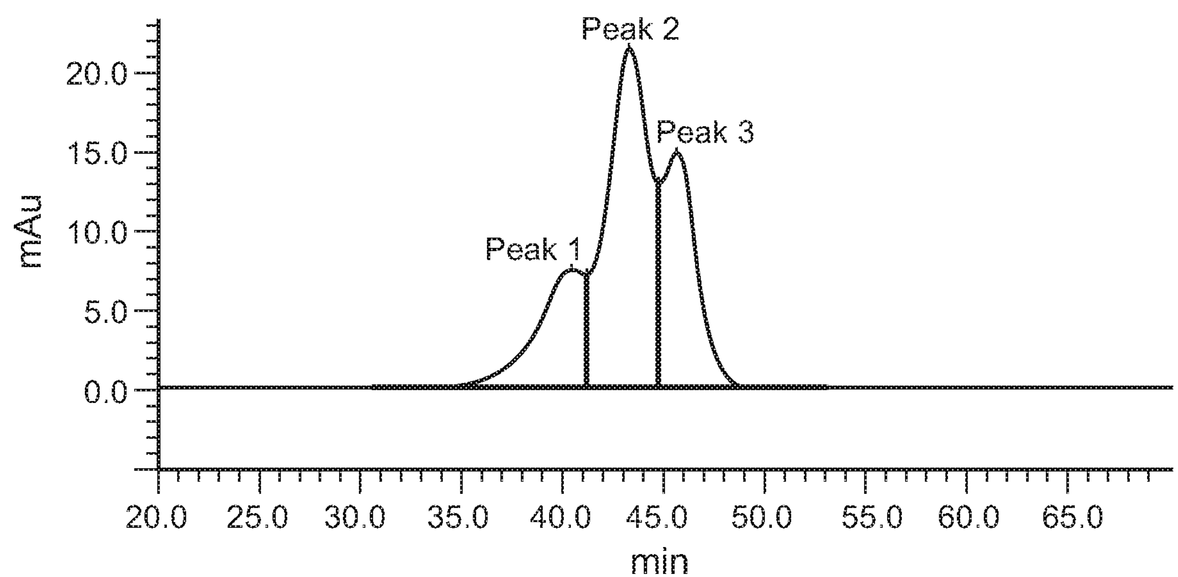
FIG. 1 Peak definition for the calculation of relative retention times on the FcRn column.
Figure 2:
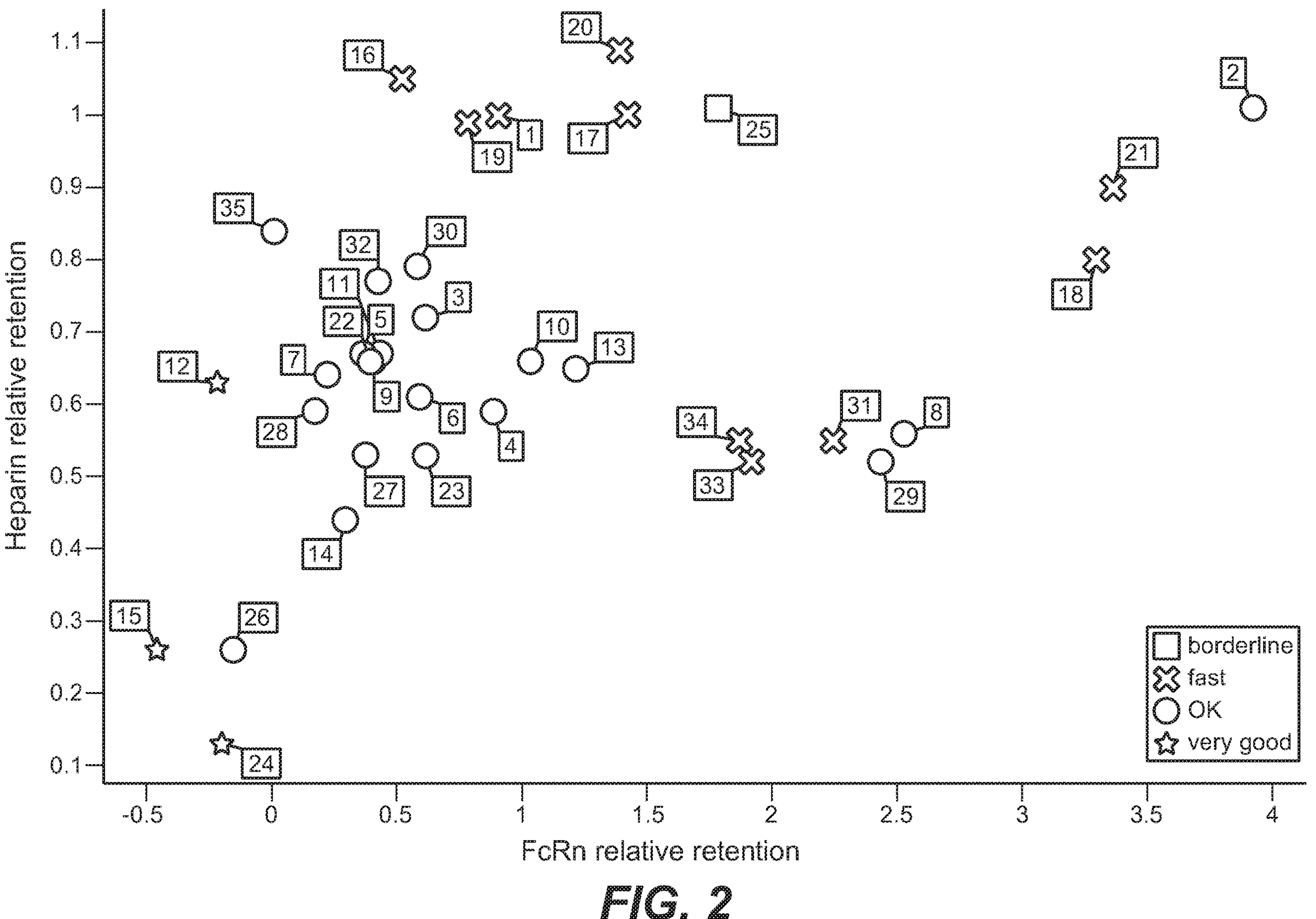
FIG. 2 FcRn relative retention plotted vs. heparin column relative retention. cross: clearance >12 mL/kg/day ("fast"); filled square: clearance between 8 and 12 mL/kg/day ("borderline"); filled circle: clearance more than 2.5 mL/kg/day but less than 8 mL/kg/day; filled star: clearance of 2.5 mL/kg/day or less.
Figure 3:
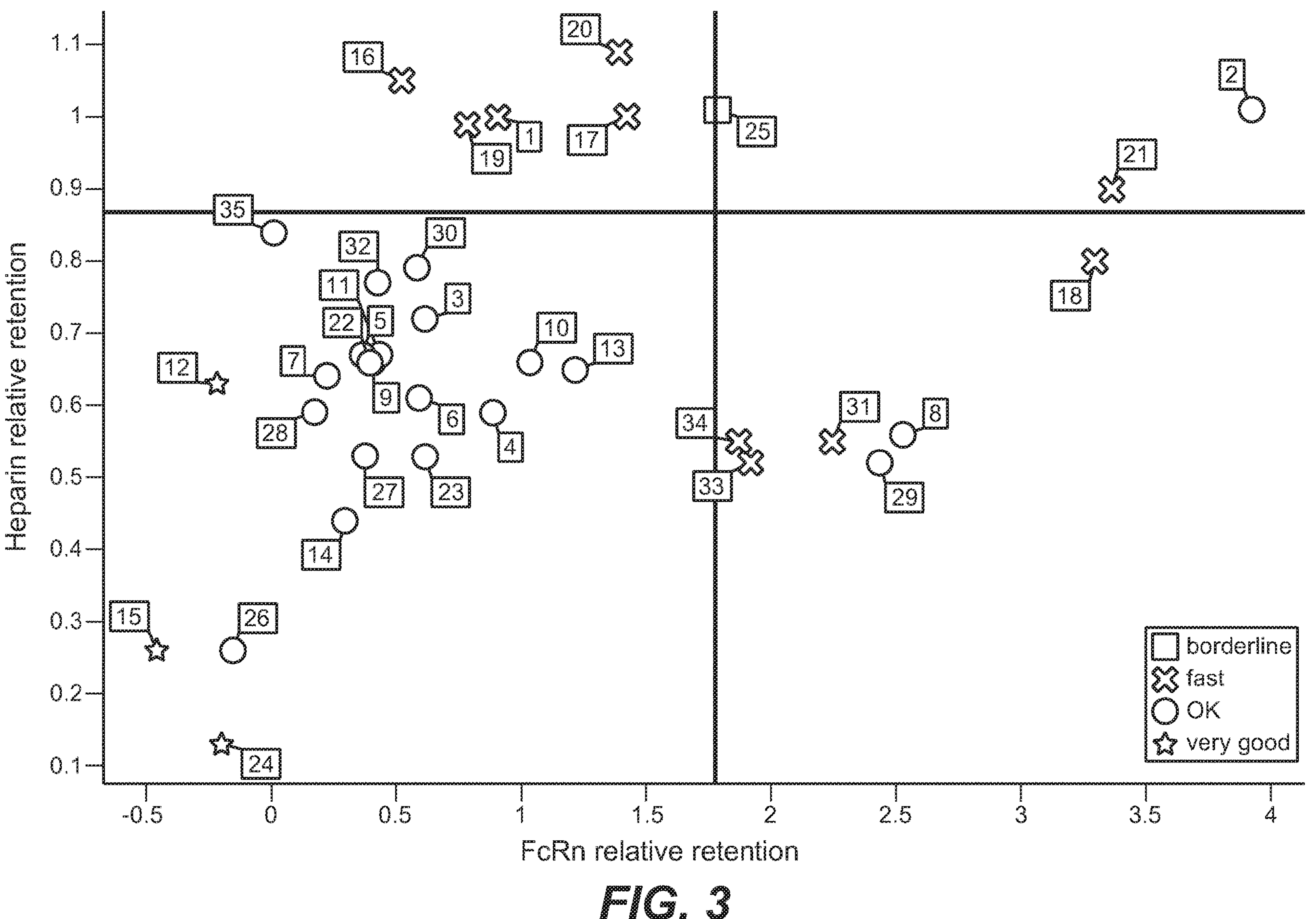
FIG. 3 FcRn relative retention plotted vs. heparin column relative retention. cross: clearance >12 mL/kg/day ("fast"); filled square: clearance between 8 and 12 mL/kg/day ("borderline"); filled circle: clearance more than 2.5 mL/kg/day but less than 8 mL/kg/day; filled star: clearance of 2.5 mL/kg/day or less; vertical lines mark the retention time ranges for therapeutically suitable clearance (lower-left quadrant, FcRn <1.78; Heparin: <0.87).
Figure 4:
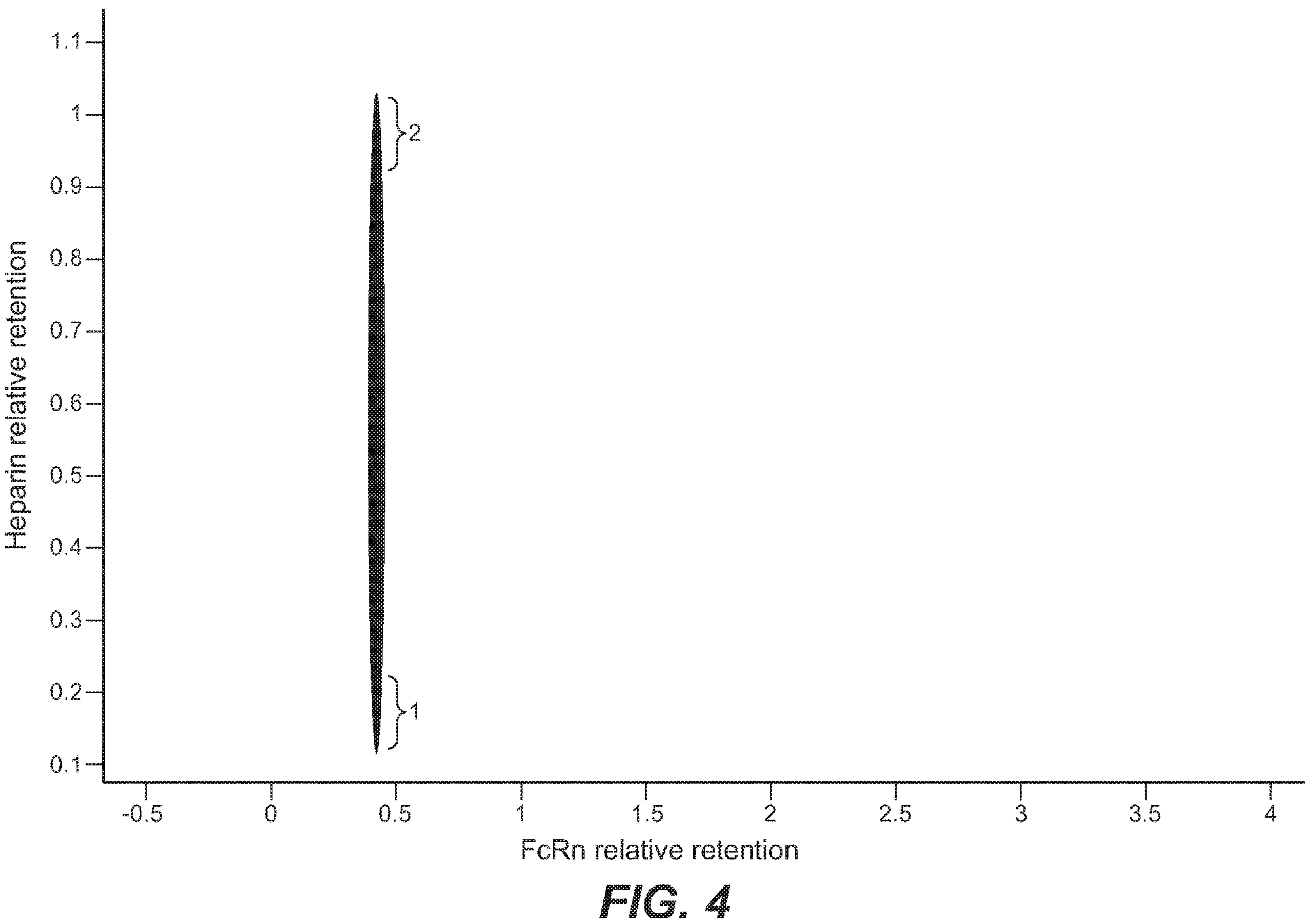
FIG. 4 FcRn relative retention plotted vs. heparin column relative retention of IVIG (intravenous immunoglobulin). 2: fraction with highest heparin binding; 1: fraction with lowest heparin binding.
Figure 5:
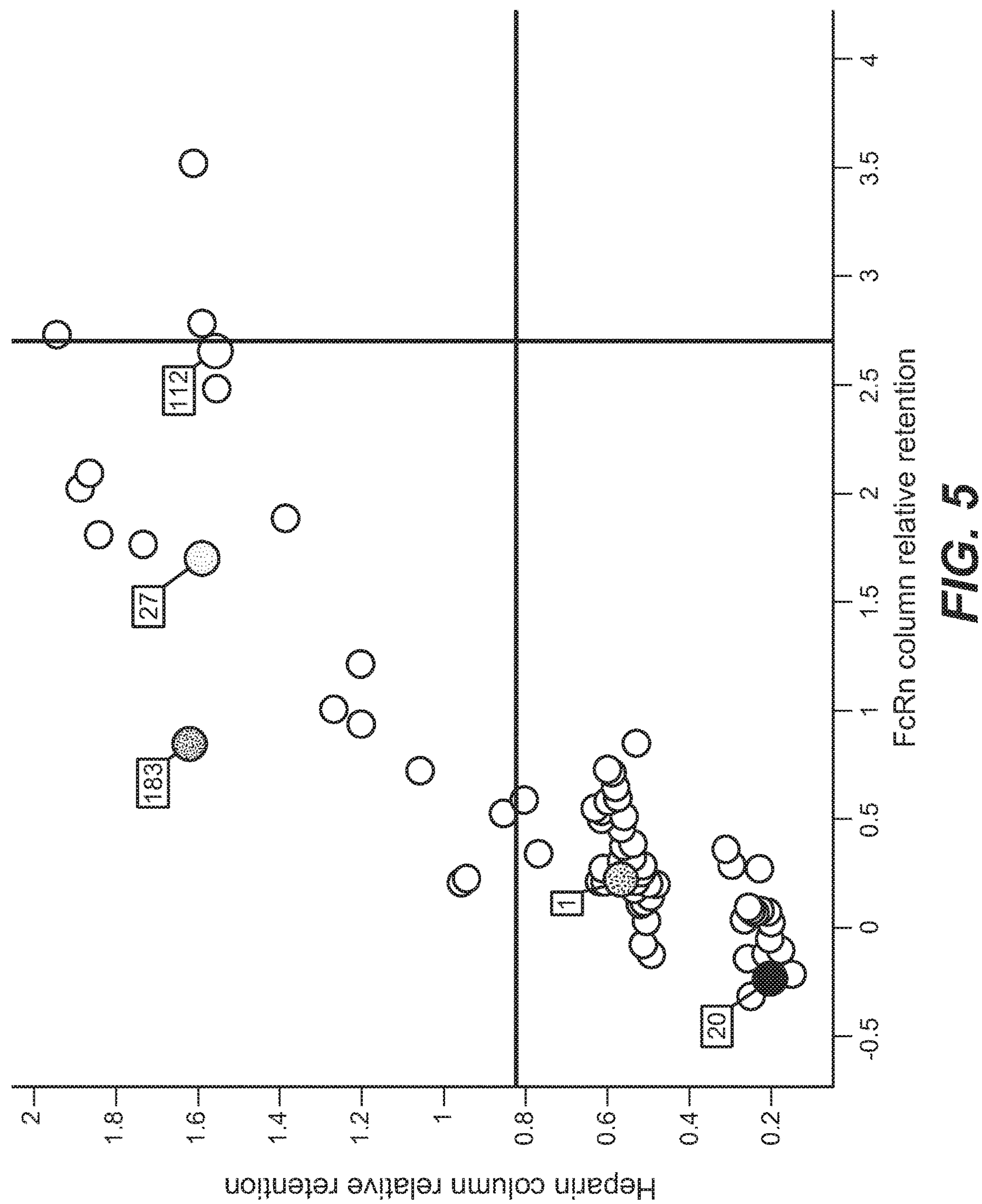
FIG. 5 FcRn relative retention plotted vs. heparin column relative retention of antibody no. 5 and variants thereof. 1: wild-type antibody; 20: negatively patched HC variant; 27: positively patched HC variant; 112: positively patched LC variant; 183: positively patched HC variant.
Figure 6:
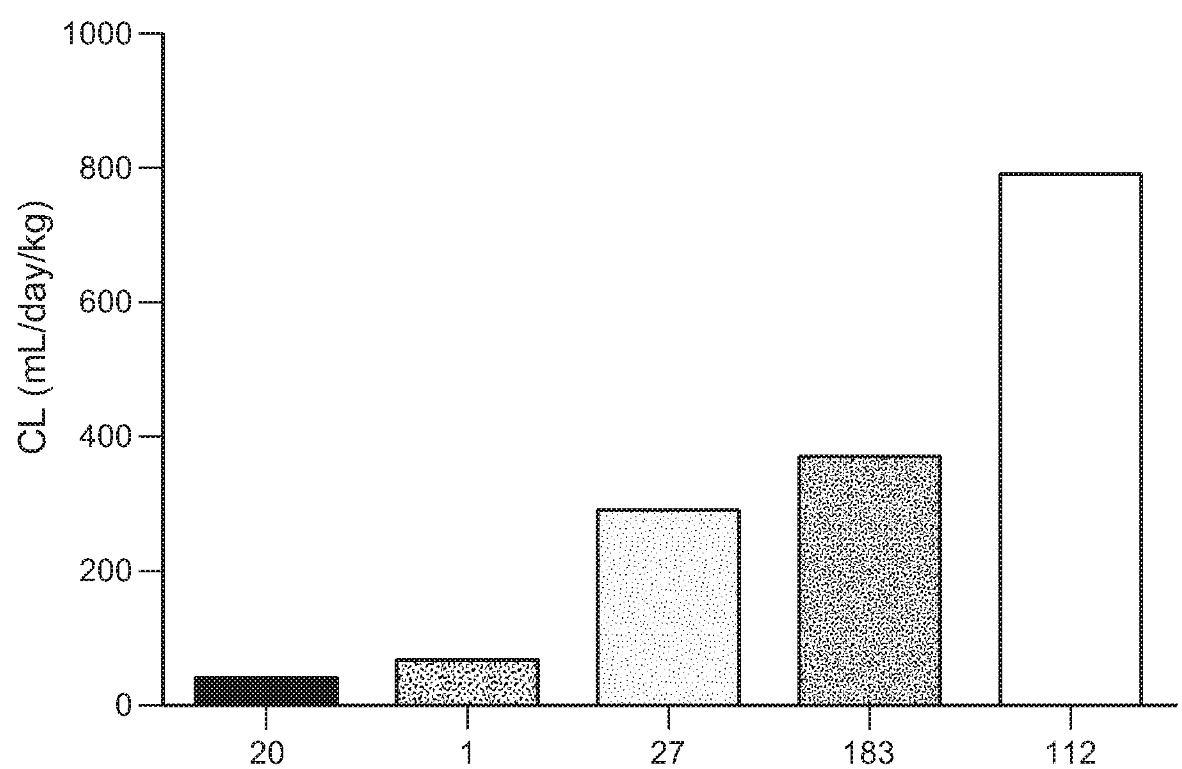
FIG. 6 Clearance of antibody no. 5 and variants thereof in FcRn knock-out mice. 1: wild-type antibody; 20: negatively patched HC variant; 27: positively patched HC variant; 112: positively patched LC variant; 183: positively patched HC variant.
Figure 7:
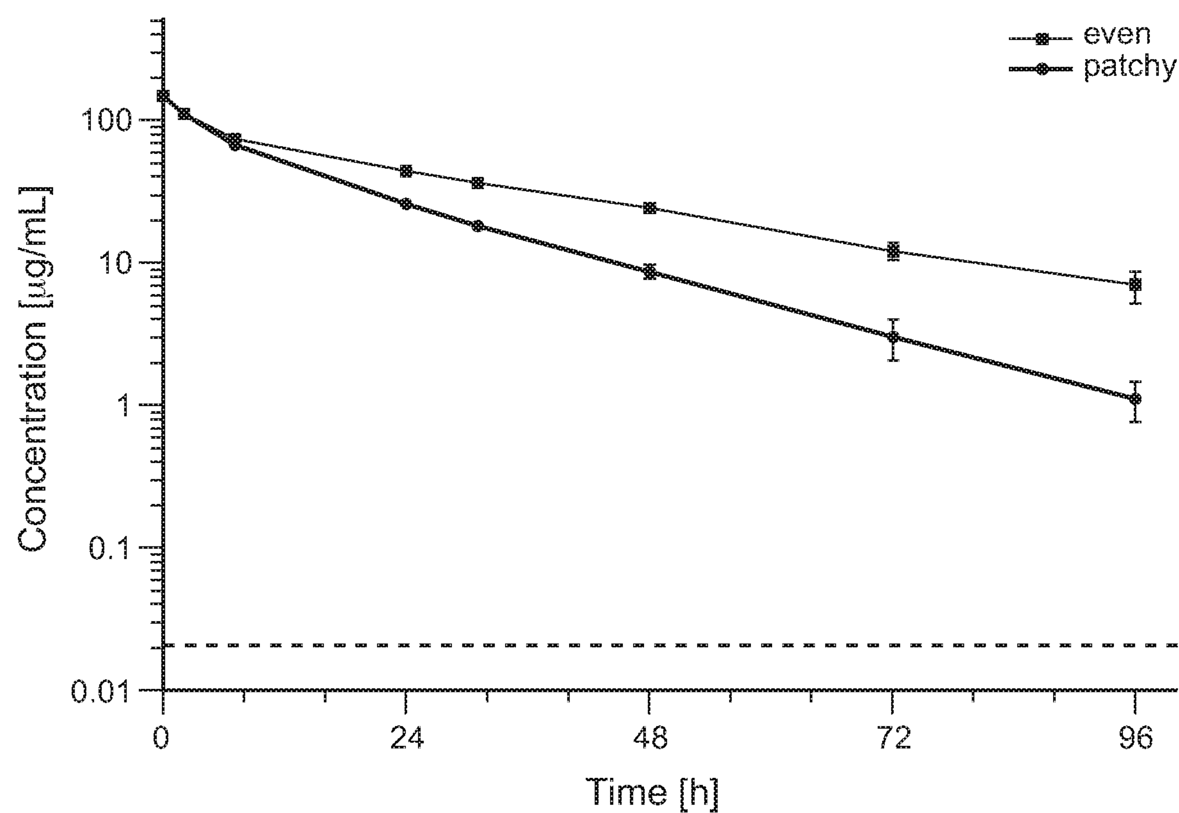
FIG. 7 Time dependent serum concentration of a non-patchy and a patchy variant of antibody no. 5 in FcRn knock-out mice.
Figure 8:
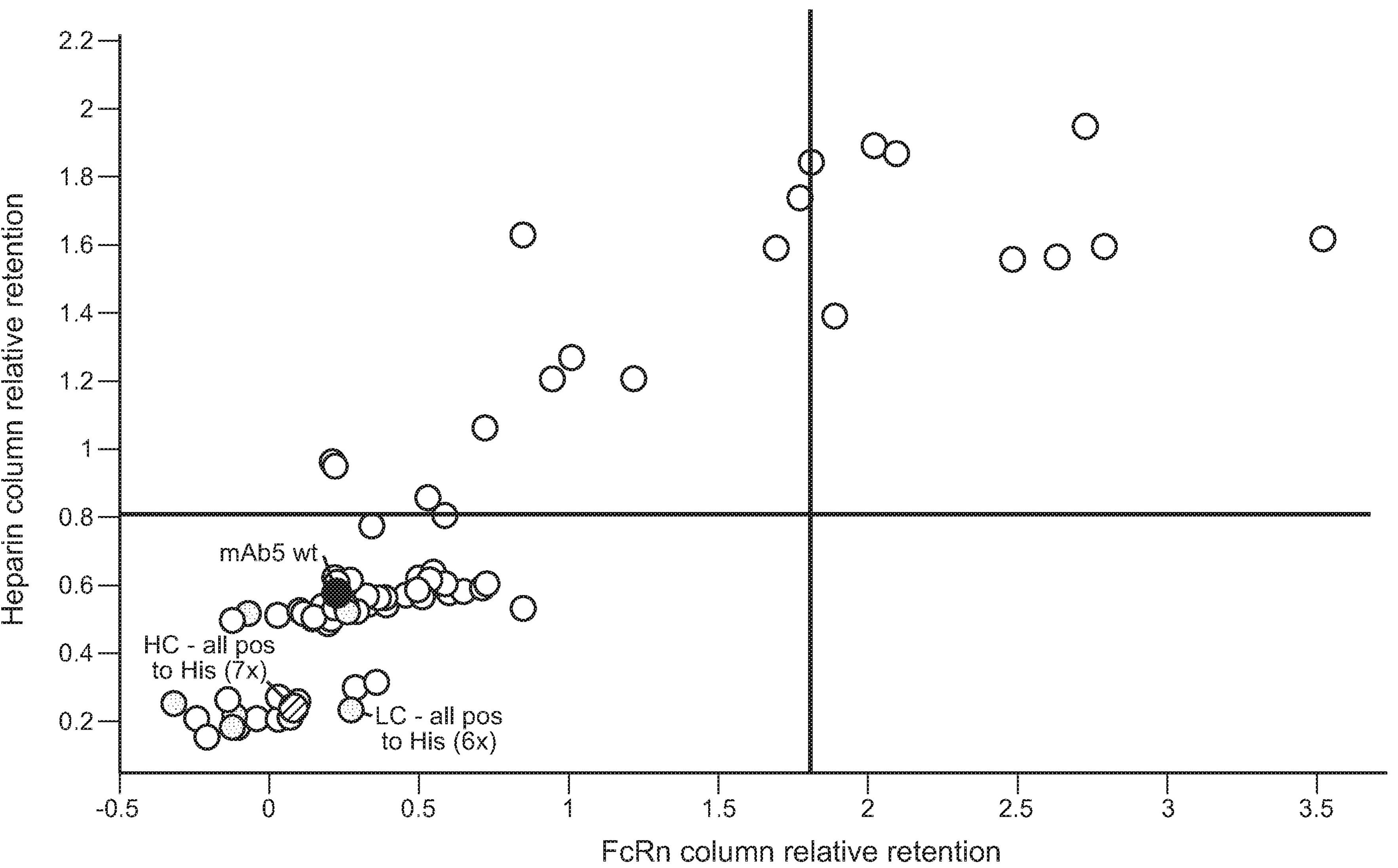
FIG. 8 FcRn relative retention plotted vs. heparin column relative retention of antibody no. 5 and histidine variants thereof.
Figure 9:
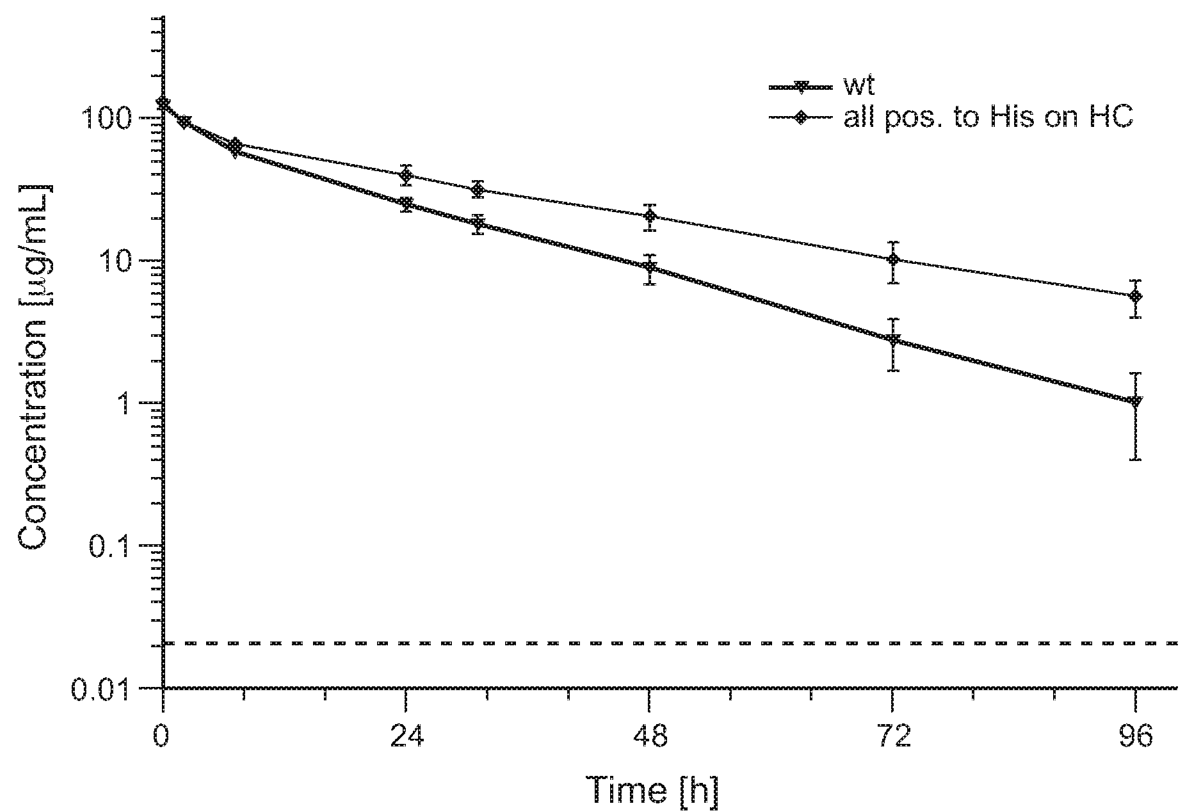
FIG. 9 Time dependent serum concentration of antibody no. 5 and a HC histidine variant thereof in FcRn knock-out mice.
Figure 10:
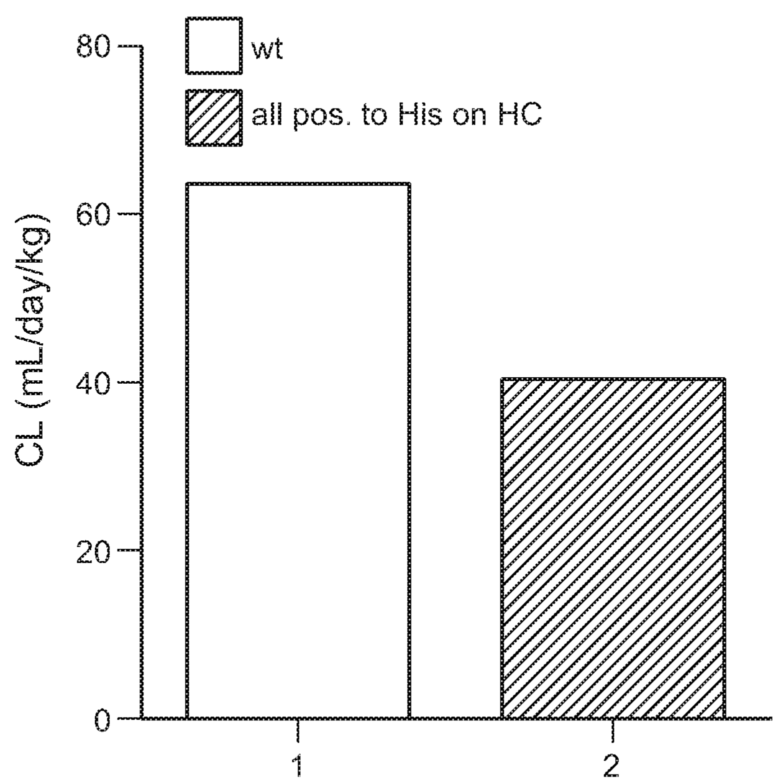
FIG. 10 Clearance of antibody no. 5 and a HC histidine variant thereof in FcRn knock-out mice.

The following examples, figures and sequences are provided to aid the understanding of the present invention, the true scope of which is set forth in the appended claims. It is understood that modifications can be made in the procedures set forth without departing from the spirit of the invention.

MATERIALS AND METHODS

Antibodies

The reference antibodies used in the experiments were an anti-pTau antibody that has the heavy chain amino acid sequence of SEQ ID NO: 01 and the light chain amino acid sequence of SEQ ID NO: 02 and an anti-Her 3 antibody that has the heavy chain amino acid sequence of SEQ ID NO: 03 and the light chain amino acid sequence of SEQ ID NO: 04.

Synthetic genes were produced at Geneart (Life technologies GmbH, Carlsbad, Calif., USA).

The monoclonal antibodies used herein were transiently expressed in HEK293 cells (see below) and purification was performed by protein A chromatography using standard procedures (see below).

The biochemical characterization included size exclusion chromatography (Waters BioSuite™ 250 7.8×300 mm, eluent: 200 mM $KH_2PO_4$, 250 mM KCl, pH 7.0) and analysis of the molecular weight distribution using the BioAnalyzer 2100 (Agilent technologies, Santa Clara, Calif., USA).

Expression Plasmids

For the expression of the above described antibodies, variants of expression plasmids for transient expression (e.g. in HEK293-F) cells based either on a cDNA organization with or without a CMV-Intron A promoter or on a genomic organization with a CMV promoter were applied.

Beside the antibody expression cassette, the plasmids contained:

- an origin of replication which allows replication of this plasmid in *E. coli,*
- a ß-lactamase gene which confers ampicillin resistance in *E. coli*, and
- the dihydrofolate reductase gene from *Mus musculus* as a selectable marker in eukaryotic cells.

The transcription unit of the antibody gene was composed of the following elements:

- unique restriction site(s) at the 5' end
- the immediate early enhancer and promoter from the human cytomegalovirus,
- followed by the Intron A sequence in the case of the cDNA organization,
- a 5'-untranslated region of a human antibody gene,
- an immunoglobulin heavy chain signal sequence,
- the human antibody chain either as cDNA or as genomic organization with the immunoglobulin exon-intron organization
- a 3' non-translated region with a polyadenylation signal sequence, and
- unique restriction site(s) at the 3' end.

The fusion genes comprising the antibody chains were generated by PCR and/or gene synthesis and assembled by known recombinant methods and techniques by connection of the according nucleic acid segments e.g. using unique restriction sites in the respective plasmids. The subcloned nucleic acid sequences were verified by DNA sequencing. For transient transfections larger quantities of the plasmids were prepared by plasmid preparation from transformed *E. coli* cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Transient Transfections in HEK293-F System

The antibodies were generated by transient transfection with the respective plasmids (e.g. encoding the heavy chain, as well as the corresponding light chain) using the HEK293-F system (Invitrogen) according to the manufacturer's instruction. Briefly, HEK293-F cells (Invitrogen) growing in suspension either in a shake flask or in a stirred fermenter in serum-free FreeStyle™ 293 expression medium (Invitrogen) were transfected with a mix of the respective expression plasmids and 293fectin™ or fectin (Invitrogen). For 2 L shake flask (Corning) HEK293-F cells were seeded at a density of $1*10^6$ cells/mL in 600 mL and incubated at 120 rpm, 8% $CO_2$. The day after the cells were transfected at a cell density of ca. $1.5*10^6$ cells/mL with ca. 42 mL mix of A) 20 mL Opti-MEM (Invitrogen) with 600 μg total plasmid DNA (1 μg/mL) encoding the heavy chain, respectively and the corresponding light chain in an equimolar ratio and B) 20 ml Opti-MEM+1.2 mL 293 fectin or fectin (2 μL/mL). According to the glucose consumption glucose solution was added during the course of the fermentation. The supernatant containing the secreted antibody was harvested after 5-10 days and antibodies were either directly purified from the supernatant or the supernatant was frozen and stored. The following antibodies have been produced accordingly:

| antibody no | format | Fc-region | antigen no. |
|---|---|---|---|
| 1 | IgG1, bivalent, monospecific, reference heparin | LALAPG | 1 |

-continued

| antibody no | format | Fc-region | antigen no. |
|---|---|---|---|
| 2 | IgG1, bivalent, monospecific | wild-type | 2 |
| 3 | IgG1, bivalent, monospecific | wild-type | 3 |
| 4 | CrossMab, bivalent, bispecific | KiH | 4 + 5 |
| 5 | IgG1, bivalent, monospecific | wild-type | 6 |
| 6 | IgG1, bivalent, monospecific | wild-type | 7 |
| 7 | IgG1, bivalent, monospecific | wild-type | 8 |
| 8 | IgG1, bivalent, monospecific | wild-type | 9 |
| 9 | IgG1, bivalent, monospecific | wild-type | 10 |
| 10 | IgG1, bivalent, monospecific, reference FcRn | wild-type | 11 |
| 11 | IgG1, bivalent, monospecific | wild-type | 12 |
| 12 | IgG4, bivalent, monospecific | wild-type | 13 |
| 13 | IgG1, bivalent, monospecific | wild-type | 9 |
| 14 | IgG1, bivalent, monospecific | wild-type | 14 |
| 15 | IgG1, bivalent, monospecific | wild-type | 15 |
| 16 | Fc-region-cytokine fusion | LALAPG | 16 |
| 17 | 2:1 heterodimeric T cell bispecific | KiH | 17 + 18 |
| 18 | 2:1 heterodimeric T cell bispecific | KiH | 9 + 18 |
| 19 | IgG1, bivalent, monospecific - cytokine fusion | KiH LALAPG | 16 + 19 |
| 20 | IgG1, bivalent, monospecific - cytokine fusion | KiH LALAPG | 16 + 17 |
| 21 | IgG1, bivalent, monospecific | wild-type | 20 + 21 |
| 22 | IgG1, bivalent, monospecific | wild-type | 20 + 21 |
| 23 | IgG1, bivalent, monospecific | wild-type | 22 |
| 24 | IgG1, bivalent, monospecific | wild-type | 23 |
| 25 | IgG1, bivalent, monospecific | wild-type | 24 |
| 26 | IgG1, bivalent, monospecific | wild-type | 25 |
| 27 | IgG1, bivalent, monospecific | wild-type | 26 |
| 28 | IgG1, bivalent, monospecific | wild-type | 27 |
| 29 | IgG1, bivalent, monospecific | wild-type | 28 |
| 30 | 2:1 heterodimeric T cell bispecific | KiH LALAPG | 29 + 18 |
| 31 | IgG1, bivalent, monospecific | wild-type | 9 |
| 32 | 2:1 heterodimeric T cell bispecific | KiH LALAPG | 17 + 18 |
| 33 | IgG1, bivalent, monospecific | LALAPG | 9 |
| 34 | IgG1-Fab fusion, trivalent, bispecific | KiH LALAPG | 9 + 30 |
| 35 | IgG1, bivalent, monospecific | wild-type | 31 |

Purification

The antibodies were purified from cell culture supernatants by affinity chromatography using MabSelectSure-Sepharose™ (GE Healthcare, Sweden), hydrophobic interaction chromatography using butyl-Sepharose (GE Healthcare, Sweden) and Superdex 200 size exclusion (GE Healthcare, Sweden) chromatography.

Briefly, sterile filtered cell culture supernatants were captured on a MabSelectSuRe resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The eluted antibody fractions were pooled and neutralized with 2 M Tris, pH 9.0. The antibody pools were prepared for hydrophobic interaction chromatography by adding 1.6 M ammonium sulfate solution to a final concentration of 0.8 M ammonium sulfate and the pH adjusted to pH 5.0 using acetic acid. After equilibration of the butyl-Sepharose resin with 35 mM sodium acetate, 0.8 M ammonium sulfate, pH 5.0, the antibodies were applied to the resin, washed with equilibration buffer and eluted with a linear gradient to 35 mM sodium acetate pH 5.0. The antibody containing fractions were pooled and further purified by size exclusion chromatography using a Superdex 200 26/60 GL (GE Healthcare, Sweden) column equilibrated with 20 mM histidine, 140 mM NaCl, pH 6.0. The antibody containing fractions were pooled, concentrated to the required concentration using Vivaspin ultrafiltration devices (Sartorius Stedim Biotech S. A., France) and stored at −80° C.

Purity and antibody integrity were analyzed after each purification step by CE-SDS using microfluidic Labchip technology (Caliper Life Science, USA). Five μl of protein solution was prepared for CE-SDS analysis using the HT Protein Express Reagent Kit according manufacturer's instructions and analyzed on LabChip GXII system using a HT Protein Express Chip. Data were analyzed using LabChip GX Software.

Mice

B6. Cg-Fcgrt$^{tmlDcr}$ Tg(FCGRT)276Dcr mice deficient in mouse FcRn α-chain gene, but hemizygous transgenic for a human FcRn α-chain gene (muFcRn−/− huFcRn tg +/−, line 276) were used for the pharmacokinetic studies. Mouse husbandry was carried out under specific pathogen free conditions. Mice were obtained from the Jackson Laboratory (Bar Harbor, Me., USA) (female, age 4-10 weeks, weight 17-22 g at time of dosing). All animal experiments were approved by the Government of Upper Bavaria, Germany (permit number 55.2-1-54-2532.2-28-10) and performed in an AAALAC accredited animal facility according to the European Union Normative for Care and Use of Experimental Animals. The animals were housed in standard cages and had free access to food and water during the whole study period.

Pharmacokinetic Studies

A single dose of antibody was injected i.v. via the lateral tail vein at a dose level of 10 mg/kg. The mice were divided into 3 groups of 6 mice each to cover 9 serum collection time points in total (at 0.08, 2, 8, 24, 48, 168, 336, 504 and 672 hours post dose). Each mouse was subjected twice to retro-orbital bleeding, performed under light anesthesia with Isoflurane™ (CP-Pharma GmbH, Burgdorf, Germany); a third blood sample was collected at the time of euthanasia. Blood was collected into serum tubes (Microvette 500Z-Gel, Sarstedt, Nümbrecht, Germany). After 2 h incubation, samples were centrifuged for 3 min at 9.300 g to obtain serum. After centrifugation, serum samples were stored frozen at −20° C. until analysis.

Determination of Human Antibody Serum Concentrations

Concentrations of Ustekinumab, Briakinumab, mAb 8 and mAb 9 in murine serum were determined by specific enzyme-linked immunoassays. Biotinylated Interleukin 12 specific to the antibodies and digoxigenin-labeled anti-human-Fc mouse monoclonal antibody (Roche Diagnostics, Penzberg, Germany) were used for capturing and detection, respectively. Streptavidin-coated microtiter plates (Roche Diagnostics, Penzberg, Germany) were coated with biotinylated capture antibody diluted in assay buffer (Roche Diagnostics, Penzberg, Germany) for 1 h. After washing, serum samples were added at various dilutions followed by another incubation step for 1 h. After repeated washings, bound human antibodies were detected by subsequent incubation with detection antibody, followed by an anti-digoxigenin antibody conjugated to horseradish peroxidase (HRP; Roche Diagnostics, Penzberg, Germany). ABTS (2,2' Azino-di[3-ethylbenzthiazoline sulfonate]; Roche Diagnostics, Germany) was used as HRP substrate to form a colored reaction product. Absorbance of the resulting reaction product was read at 405 nm with a reference wavelength at 490 nm using a Tecan sunrise plate reader (Männedorf, Switzerland).

All serum samples, positive and negative control samples were analyzed in duplicates and calibrated against reference standard.

Pharmacokinetic (PK) Analysis

The pharmacokinetic parameters were calculated by non-compartmental analysis using WinNonlin™ 1.1.1 (Pharsight, Calif., USA).

Briefly, area under the curve ($AUCo_{0-inf}$) values were calculated by logarithmic trapezoidal method due to non-linear decrease of the antibodies and extrapolated to infinity using the apparent terminal rate constant λz, with extrapolation from the observed concentration at the last time point.

Plasma clearance was calculated as Dose rate (D) divided by $AUCo_{0-inf}$. The apparent terminal half-life (T1/2) was derived from the equation T1/2=ln2/λz.

EXAMPLE 1

Preparation of FcRn Affinity Column

Expression of FcRn in HEK293 Cells

FcRn was transiently expressed by transfection of HEK293 cells with two plasmids containing the coding sequence of FcRn and of beta-2-microglobulin. The transfected cells were cultured in shaker flasks at 36.5° C., 120 rpm (shaker amplitude 5 cm), 80% humidity and 7% $CO_2$. The cells were diluted every 2-3 days to a density of 3 to $4*10^5$ cells/ml.

For transient expression, a 14 l stainless steel bioreactor was started with a culture volume of 8 liters at 36.5° C., pH 7.0±0.2, $pO_2$ 35% (gassing with $N_2$ and air, total gas flow 200 ml $min^{-1}$) and a stirrer speed of 100-400 rpm. When the cell density reached $20*10^5$ cells/ml, 10 mg plasmid DNA (equimolar amounts of both plasmids) was diluted in 400 ml Opti-MEM (Invitrogen). 20 ml of 293 fectin (Invitrogen) was added to this mixture, which was then incubated for 15 minutes at room temperature and subsequently transferred into the fermenter. From the next day on, the cells were supplied with nutrients in continuous mode: a feed solution was added at a rate of 500 ml per day and glucose as needed to keep the level above 2 g/l. The supernatant was harvested 7 days after transfection using a swing head centrifuge with 1 l buckets: 4000 rpm for 90 minutes. The supernatant (13 L) was cleared by a Sartobran P filter (0.45 μm+0.2 μm, Sartorius) and the FcRn beta-2-microglobulin complex was purified therefrom.

Biotinylation of Neonatal Fc Receptor 3 mg FcRn beta-2-microglobulin complex were solved/diluted in 5.3 mL 20 mM sodium dihydrogenphosphate buffer containing 150 mM sodium chloride and added to 250 μl PBS and 1 tablet complete protease inhibitor (complete ULTRA Tablets, Roche Diagnostics GmbH). FcRn was biotinylated using the biotinylation kit from Avidity according to the manufacturer instructions (Bulk BIRA, Avidity LLC). The biotinylation reaction was done at room temperature overnight.

The biotinylated FcRn was dialyzed against 20 mM MES buffer comprising 140 mM NaCl, pH 5.5 (buffer A) at 4° C. overnight to remove excess of biotin.

Coupling to Streptavidin Sepharose

For coupling to streptavidin sepharose, 1 mL streptavidin sepharose (GE Healthcare, United Kingdom) was added to the biotinylated and dialyzed FcRn beta-2-microglobulin complex and incubated at 4° C. overnight. The FcRn beta-2-microglobulin complex derivatized sepharose was filled a 4.6 mm×50 mm chromatographic column (Repligen). The column was stored in 80% buffer A and 20% buffer B (20 mM Tris(hydroxymethyl)aminomethane pH 8.8, 140 mM NaCl).

EXAMPLE 2

Chromatography Using FcRn Affinity Column and pH Gradient

Conditions column dimensions: 50 mm×4.6 mm
loading: 30 μg sample
buffer A: 20 mM MES, with 140 mM NaCl, adjusted to pH 5.5
buffer B: 20 mM Tris/HC1, with 140 mM NaCl, adjusted to pH 8.8

30 μl of samples were applied onto the FcRn affinity column equilibrated with buffer A. After a washing step of 10 minutes in 20% buffer B at a flow rate of 0.5 mL/min, elution was performed with a linear gradient from 20% to 70% buffer B over 70 minutes. The UV light absorption at a wavelength of 280 nm was used for detection. The column was regenerated for 10 minutes using 20% buffer B after each run.

For the calculation of relative retention times, a standard sample (anti-Her3 antibody (SEQ ID NO: 03 and 04), oxidized for 18 hours with 0.02% hydrogen peroxide according to (Bertoletti-Ciarlet, A., et al., Mol. Immunol. 46 (2009) 1878-1882) was run at the beginning of a sequence and after each 10 sample injections.

Briefly, the antibody (at 9 mg/mL) in 10 mM sodium phosphate pH 7.0 was mixed with H2O2 to a final concentration of 0.02% and incubated at room temperature for 18 h. To quench the reaction, the samples were thoroughly dialyzed into pre-cooled 10 mM sodium acetate buffer pH 5.0.

Relative retention times were calculated according to the following equation:

$$t_{rel,i} = \frac{t_i - t_{peak2}}{t_{peak3} - t_{peak2}}$$

For peak definition see FIG. 1.

EXAMPLE 3

Chromatography Using Heparin Affinity Column and pH Gradient

Conditions column dimensions: 50 mm×5.0 mm
loading: 20-50 μg sample buffer A: 50 mM TRIS pH 7.4 buffer B: 50 mM TRIS pH 7.4, 1000 mM NaCl 20 to 50 μg of protein samples in low-salt buffer (≤25 mM ionic strength) were applied to a TSKgel Heparin-5PW Glass column, 5.0×50 mm (Tosoh Bioscience, Tokyo/Japan), which was pre-equilibrated with buffer A at room temperature. Elution was performed with a linear gradient from 0-100% buffer B over 32 minutes at a flow rate of 0.8 mg/mL. The UV light absorption at a wavelength of 280 nm was used for detection. Every injection sequence started with a retention time standard (anti-pTau antibody) which was used to calculate relative retention times according to the following formula:

$$t_{rel,i} = \frac{t_i}{t_{pTau}}$$

($t_{rel,i}$: relative retention time of peak i; $t_i$: retention time of peak i; $t_{pTau}$: retention time of the anti-pTau antibody peak).

EXAMPLE 4

Cynomolgus SDPK Studies

The pharmacokinetics of the test compounds was determined in cynomolgus monkeys following single intravenous administration at dose levels ranging from 0.3 mg/kg to 150 mg/kg. Serial blood samples were collected from the monkeys over several weeks and serum/plasma was prepared from the collected blood samples. Serum/plasma levels of test compounds were determined by ELISA. In case of linear pharmacokinetics pharmacokinetic parameter were determined by standard non-compartmental methods. Clearance was calculated according to following formula:

Clearance=Dose/Area under concentration-time curve

In cases of non-linear pharmacokinetics, the linear fraction of the clearance was determined via following alternative methods: Either clearance values were estimated following IV administration at high dose levels, at which additional non-linear clearance pathways are virtually saturated. Alternatively, PK models comprising a linear and a non-linear, saturable clearance term were established. In these cases, the model-determined linear clearance fraction was used for correlations.

Results

| antibody no | heparin affinity column rel. retention (vs. pTau) | FcRn affinity column rel. retention (vs. Her3 Pre-peak 1 and Main Peak) | clearance* [mL/kg/day] |
|---|---|---|---|
| 1 | 1 | 0.9 | 61.1 |
| 2 | 1.01 | 3.92 | 5.01 |
| 3 | 0.72 | 0.61 | 3.34 |
| 4 | 0.59 | 0.88 | 3.97 |
| 5 | 0.67 | 0.36 | 3.47 |
| 6 | 0.61 | 0.59 | 5.13 |
| 7 | 0.64 | 0.22 | 6.41 |
| 8 | 0.56 | 2.52 | 4.1 |
| 9 | 0.66 | 0.4 | 5.28 |
| 10 | 0.66 | 1.03 | 4.1 |
| 11 | 0.67 | 0.43 | 5.52 |
| 12 | 0.63 | −0.22 | 1.6 |
| 13 | 0.65 | 1.21 | <8 |
| 14 | 0.44 | 0.29 | 4.73 |
| 15 | 0.26 | −0.46 | 2.4 |
| 16 | 1.05 | 0.52 | >12 |
| 17 | 1 | 1.42 | 24.9 |
| 18 | 0.8 | 3.29 | 90 |
| 19 | 0.99 | 0.78 | 17 |
| 20 | 1.09 | 1.39 | 16.4 |
| 21 | 0.9 | 3.36 | >8 |
| 22 | 0.66 | 0.39 | >8 |
| 23 | 0.53 | 0.61 | 5.37 |
| 24 | 0.13 | −0.199 | 2.5 |
| 25 | 1.01 | 1.78 | 8.16 |
| 26 | 0.26 | −0.16 | 4.81 |
| 27 | 0.53 | 0.37 | 2.45 |
| 28 | 0.59 | 0.17 | 4.8 |
| 29 | 0.52 | 2.43 | 4.87 |
| 30 | 0.79 | 0.58 | 6.3 |
| 31 | 0.55 | 2.24 | 31.92 |
| 32 | 0.77 | 0.42 | 7.5 |
| 33 | 0.52 | 1.91 | 10.08 |
| 34 | 0.55 | 1.86 | 31.92 |
| 35 | 0.84 | 0.01 | 4.63 |

The invention claimed is:

1. A method for selecting an antibody with a systemic clearance in cynomolgus monkeys of less than 8 mL/kg/day comprising the following steps:

a) measuring the retention time of the antibody on an FcRn affinity chromatography column with a positive linear pH gradient and on a heparin affinity chromatography column with a positive linear conductivity/salt gradient, wherein the pH gradient is from a first pH value to a second pH value whereby the first pH value is from pH 3.5 to pH 6.4 and the second pH value is from pH 7.4 to pH 9.5, and wherein the conductivity/salt gradient is performed with buffer A of 50 mM TRIS pH 7.4 and buffer B of 50 mM TRIS pH 7.4, 1000 mM NaCl, and b) selecting the antibody i) if the relative retention time on the FcRn affinity chromatography column is less than 1.78 times the retention time difference between peaks 2 and 3 of a preparation of an oxidized anti-Her3 antibody of SEQ ID NO: 3 and 4, and ii) if the relative retention time on the heparin affinity chromatography column is less than 0.87 times the retention time of an anti-pTau antibody of SEQ ID NO: 1 and 2.

2. The method according to claim 1, wherein the antibody is selected from the group consisting of a full length antibody, a CrossMab, a 2:1 heterodimeric T cell bispecific antibody, an antibody-cytokine fusion polypeptide, an Fc-region-cytokine fusion polypeptide, and an antibody-Fab fusion polypeptide.

3. The method according to claims 1 or 2, wherein the antibody comprises an Fc-region selected from the group consisting of a human IgG1 Fc-region, a human IgG1 Fc-region with the mutations L234A, L235A and P329G, a human IgG1 Fc-region with the knob-into-hole mutations, and combinations thereof.

4. The method according to claims 1 or 2, wherein an immobilized non-covalent complex of a neonatal Fc receptor (FcRn) and beta-2-microglobulin (b2m) as affinity chromatography ligand is used in the FcRn affinity chromatography with a positive linear pH gradient, wherein the non-covalent complex of the neonatal Fc receptor and beta-2-microglobulin is bound to a chromatography material and the non-covalent complex is conjugated to the solid phase via a specific binding pair, and wherein the non-covalent complex of the neonatal Fc receptor (FcRn) and beta-2-microglobulin (b2m) is mono-biotinylated and the solid phase is derivatized with streptavidin.

5. The method according to claim 4, wherein the pH gradient is from a first pH value to a second pH value whereby the first pH value is pH 5.5 and the second pH value is pH 8.8.

6. The method according to claims 1 or 2, wherein the relative retention time on the FcRn affinity chromatography column is calculated according to the following equation:

$$t_{rel,i} = \frac{t_i - t_{peak2}}{t_{peak3} - t_{peak2}}$$

based on the peak definition according to $t_{rel,i}$: relative retention time of peak i; $t_i$; retention time of peak i; $t_{peak2}$; retention time of the peak of the partially oxidized anti-Her3 antibody; $t_{peak3}$: retention time of the peak of the non-oxidized anti-Her3 antibody.

7. The method according to claims 1 or 2, wherein the relative retention time on the heparin affinity chromatography column is calculated according to the following formula:

$$t_{rel,i} = \frac{t_i}{t_{pTau}}$$

($t_{rel,i}$: relative retention time of peak i; $t_i$: retention time of peak i; $t_{pTau}$: retention time of the anti-pTau antibody peak).

* * * * *

SEQUENCE LISTING

```
<160> NUMBER OF SEQ ID NOS: 33

<210> SEQ ID NO 1
<211> LENGTH: 441
<212> TYPE: PRT
<213> ORGANISM: Artificial Sequence
<220> FEATURE:
<223> OTHER INFORMATION: anti-pTau antibody HC

<400> SEQUENCE: 1

Glu Val Gln Val Leu Glu Ser Gly Gly Gly Leu Val Gln Pro Gly Gly
1               5                   10                  15

Ser Leu Arg Leu Ser Cys Ala Val Ser Gly Phe Ser Leu Ser Ser Asn
            20                  25                  30

Ala Ile Asn Trp Val Arg Gln Ala Pro Gly Lys Gly Leu Glu Trp Val
        35                  40                  45
```

```
Gly Tyr Ile Ala Val Ser Gly Asn Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Gly Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 2
<211> LENGTH: 218
```

<212> TYPE: PRT
<213> ORGANISM: Artificial Sequence
<220> FEATURE:
<223> OTHER INFORMATION: anti-pTau antibody LC

<400> SEQUENCE: 2

```
Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Tyr Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ala Asp Ile Val Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 3
<211> LENGTH: 449
<212> TYPE: PRT
<213> ORGANISM: Artificial Sequence
<220> FEATURE:
<223> OTHER INFORMATION: anti-Her3 antibody HC

<400> SEQUENCE: 3

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Ser
            20                  25                  30

Tyr Ile Ser Trp Val Arg Gln Ala Pro Gly Gln Gly Leu Glu Trp Met
        35                  40                  45

Gly Trp Ile Tyr Ala Gly Thr Gly Ser Pro Ser Tyr Asn Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Arg Asp Tyr Tyr Ser Asn Ser Leu Thr Tyr Trp Gly Gln
            100                 105                 110
```

```
Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 4
<211> LENGTH: 220
<212> TYPE: PRT
<213> ORGANISM: Artificial Sequence
<220> FEATURE:
<223> OTHER INFORMATION: anti-Her3 antibody LC

<400> SEQUENCE: 4

```
Asp Ile Val Met Thr Gln Ser Pro Asp Ser Leu Ala Val Ser Leu Gly
1               5                   10                  15
```

```
Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 5
<211> LENGTH: 227
<212> TYPE: PRT
<213> ORGANISM: Homo sapiens

<400> SEQUENCE: 5

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 6
<211> LENGTH: 326
<212> TYPE: PRT
<213> ORGANISM: Homo sapiens

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
```

```
305                 310                 315                 320

Ser Leu Ser Pro Gly Lys
                325


<210> SEQ ID NO 7
<211> LENGTH: 377
<212> TYPE: PRT
<213> ORGANISM: Homo sapiens

<400> SEQUENCE: 7

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350
```

```
Phe Ser Cys Ser Val Met His Glu Ala Leu His Asn Arg Phe Thr Gln
        355                 360                 365

Lys Ser Leu Ser Leu Ser Pro Gly Lys
    370                 375


<210> SEQ ID NO 8
<211> LENGTH: 229
<212> TYPE: PRT
<213> ORGANISM: Homo sapiens

<400> SEQUENCE: 8

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 9
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with the mutations L234A, L235A

<400> SEQUENCE: 9

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45
```

```
Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 10
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with Y349C, T366S, L368A and Y407V mutations

<400> SEQUENCE: 10

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 11
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with S354C, T366W mutations

<400> SEQUENCE: 11

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 12
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A mutations and Y349C, T366S, L368A,
      Y407V mutations
```

<400> SEQUENCE: 12

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 13
<211> LENGTH: 227
<212> TYPE: PRT
<213> ORGANISM: Artificial Sequence
<220> FEATURE:
<223> OTHER INFORMATION: human IgG1 Fc-region derived Fc-region polypeptide with a L234A, L235A and S354C, T366W mutations

<400> SEQUENCE: 13

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

```
Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 14
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a P329G mutation

<400> SEQUENCE: 14

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

```
<210> SEQ ID NO 15
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A mutations and P329G mutation

<400> SEQUENCE: 15

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 16
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a P239G mutation and Y349C, T366S, L368A, Y407V
      mutations

<400> SEQUENCE: 16

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
```

```
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 17
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a P329G mutation and S354C, T366W mutation

<400> SEQUENCE: 17

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 18
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A, P329G and Y349C, T366S, L368A,
      Y407V mutations

<400> SEQUENCE: 18

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 19
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A, P329G mutations and S354C, T366W
      mutations
```

<400> SEQUENCE: 19

Asp Lys Thr His Thr Cys Pro Pro Cys Pro Ala Pro Glu Ala Ala Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Gly Ala Pro Ile
100 105 110

Glu Lys Thr Ile Ser Lys Ala Lys Gly Gln Pro Arg Glu Pro Gln Val
115 120 125

Tyr Thr Leu Pro Pro Cys Arg Asp Glu Leu Thr Lys Asn Gln Val Ser
130 135 140

Leu Trp Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 20
<211> LENGTH: 229
<212> TYPE: PRT
<213> ORGANISM: Artificial Sequence
<220> FEATURE:
<223> OTHER INFORMATION: human IgG4 Fc-region derived Fc-region polypeptide with S228P and L235E mutations

<400> SEQUENCE: 20

Glu Ser Lys Tyr Gly Pro Pro Cys Pro Pro Cys Pro Ala Pro Glu Phe
1 5 10 15

Glu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

```
Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 21
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S228P, L235E mutations and P329G mutation

<400> SEQUENCE: 21

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

-continued

<210> SEQ ID NO 22
<211> LENGTH: 229
<212> TYPE: PRT
<213> ORGANISM: Artificial Sequence
<220> FEATURE:
<223> OTHER INFORMATION: human IgG4 Fc-region derived Fc-region polypeptide with S354C, T366W mutations

<400> SEQUENCE: 22

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 23
<211> LENGTH: 229
<212> TYPE: PRT
<213> ORGANISM: Artificial Sequence
<220> FEATURE:
<223> OTHER INFORMATION: human IgG4 Fc-region derived Fc-region polypeptide with Y349C, T366S, L368A, Y407V mutations

<400> SEQUENCE: 23

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60
```

```
Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 24
<211> LENGTH: 229
<212> TYPE: PRT
<213> ORGANISM: Artificial Sequence
<220> FEATURE:
<223> OTHER INFORMATION: human IgG4 Fc-region derived Fc-region polypeptide with a S228P, L235E and S354C, T366W mutations

<400> SEQUENCE: 24

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
```

```
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 25
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E and Y349C, T366S, L368A, Y407V
      mutations

<400> SEQUENCE: 25

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 26
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P329G mutation

<400> SEQUENCE: 26
```

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 27
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P239G and Y349C, T366S, L368A, Y407V mutations

<400> SEQUENCE: 27

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125
```

```
Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 28
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P329G and S354C, T366W mutations

<400> SEQUENCE: 28

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 29
<211> LENGTH: 229
<212> TYPE: PRT
<213> ORGANISM: Artificial Sequence
<220> FEATURE:
<223> OTHER INFORMATION: human IgG4 Fc-region derived Fc-region polypeptide with a S228P, L235E, P329G and Y349C, T366S, L368A, Y407V mutations

<400> SEQUENCE: 29

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 30
<211> LENGTH: 229
<212> TYPE: PRT
<213> ORGANISM: Artificial Sequence
<220> FEATURE:
<223> OTHER INFORMATION: human IgG4 Fc-region derived Fc-region polypeptide with a S228P, L235E, P329G and S354C, T366W mutations

<400> SEQUENCE: 30

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60
```

```
Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

```
<210> SEQ ID NO 31
<211> LENGTH: 274
<212> TYPE: PRT
<213> ORGANISM: Homo sapiens

<400> SEQUENCE: 31

Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
            20                  25                  30

Gln Gln Tyr Leu Ser Tyr Asn Ser Leu Arg Gly Glu Ala Glu Pro Cys
        35                  40                  45

Gly Ala Trp Val Trp Glu Asn Gln Val Ser Trp Tyr Trp Glu Lys Glu
    50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
        115                 120                 125

Gly Asp Trp Pro Glu Ala Leu Ala Ile Ser Gln Arg Trp Gln Gln Gln
    130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
            180                 185                 190

Phe Ser Val Leu Thr Cys Ser Ala Phe Ser Phe Tyr Pro Pro Glu Leu
        195                 200                 205
```

-continued

```
Gln Leu Arg Phe Leu Arg Asn Gly Leu Ala Ala Gly Thr Gly Gln Gly
    210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu Glu Ser Pro Ala Lys
            260                 265                 270

Ser Ser


<210> SEQ ID NO 32
<211> LENGTH: 21
<212> TYPE: PRT
<213> ORGANISM: Artificial Sequence
<220> FEATURE:
<223> OTHER INFORMATION: HIS-AVITAG

<400> SEQUENCE: 32

His His His His His His Gly Leu Asn Asp Ile Phe Glu Ala Gln Lys
1               5                   10                  15

Ile Glu Trp His Glu
            20


<210> SEQ ID NO 33
<211> LENGTH: 99
<212> TYPE: PRT
<213> ORGANISM: Homo sapiens

<400> SEQUENCE: 33

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met
```